United States Patent [19]
Coolidge et al.

[11] Patent Number: 5,595,887
[45] Date of Patent: Jan. 21, 1997

[54] PURIFICATION DIRECTED CLONING OF PEPTIDES USING CARBONIC ANHYDRASE AS THE AFFINITY BINDING SEGMENT

[75] Inventors: Thomas R. Coolidge, Falls Village, Conn.; Fred Wagner, Walton, Nebr.; Gino van Heeke; Sheldon M. Schuster, both of Gainesville, Fla.; Jay Stout; Dwane E. Wylie, both of Lincoln, Nebr.

[73] Assignee: BioNebraska, Inc., Lincoln, Nebr.

[21] Appl. No.: 552,810

[22] Filed: Jul. 16, 1990

[51] Int. Cl.$^6$ .............................. C12P 21/04; C12P 21/06
[52] U.S. Cl. ......................... 435/69.7; 435/68.1
[58] Field of Search ................... 435/69.7, 68.1, 435/69.8, 69.1

[56] References Cited

U.S. PATENT DOCUMENTS

| | | | |
|---|---|---|---|
| 4,543,329 | 9/1985 | Daum et al. | 435/69.7 |
| 4,703,004 | 10/1987 | Hopp et al. | 435/68 |
| 4,745,051 | 5/1988 | Smith et al. | 435/68 |
| 4,769,326 | 9/1988 | Rutter | 435/69.7 |
| 4,782,137 | 11/1988 | Hopp et al. | 530/328 |
| 4,801,536 | 1/1989 | Stahl et al. | 435/69.8 |
| 4,816,397 | 3/1989 | Boss et al. | 435/68 |
| 4,931,498 | 6/1990 | Pidgeon | 525/54.1 |
| 5,013,653 | 5/1991 | Huston et al. | 435/69.7 |
| 5,053,133 | 10/1991 | Klein et al. | 210/500.38 |
| 5,093,241 | 3/1992 | Bennett et al. | 435/69.4 |
| 5,116,750 | 5/1992 | Gelfand et al. | 435/193 |
| 5,168,049 | 12/1992 | Meade et al. | 435/69.1 |

FOREIGN PATENT DOCUMENTS

| | | |
|---|---|---|
| 0131363 | 1/1985 | European Pat. Off. . |
| 0163406 | 12/1985 | European Pat. Off. . |
| 0230869 | 8/1987 | European Pat. Off. . |
| 0244147 | 11/1987 | European Pat. Off. . |
| 0286239 | 10/1988 | European Pat. Off. . |
| 0327522 | 8/1989 | European Pat. Off. . |
| 0333691 | 9/1989 | European Pat. Off. . |
| 3523701 | 1/1987 | Germany . |
| 62-283998 | 12/1987 | Japan . |
| 2162190 | 1/1986 | United Kingdom . |
| 2180539 | 4/1987 | United Kingdom . |
| WO86/02077 | 4/1986 | WIPO . |
| 8807085 | 9/1988 | WIPO . |

OTHER PUBLICATIONS

Whitney (1974) *Anal. Biochem.*, 57, 467–476.
Osborne et al. (1975) *Anal. Biochem.*, 64, 297–303.
Moks et al. (1987) *Biochemistry*, 26, 5239–5244.
Nilsson et al. (1985) *Nucl. Acids Res.*, 13(4), 1151–1162.
Olson et al. (1988) *Peptides*, 9, 301, 307.
Sapirstein (1985) *Res. Methods Neurochem.*, 6, 245–262 in *Chem. Abst*, 103, 243, Abst #2604U.
Carter (1990) "Site-Specific Proteolysis of Fusion Proteins" in ACS Symposium Series 427, *Protein Purification from Molecular Mechanisms to Large–Scale Processes'*, Ladish (ed.), ACS Washington DC, pp. 181–193.
Hanada et al. (1988) *J. Biol. Chem.*, 263(15), 7181–7185.

(List continued on next page.)

*Primary Examiner*—Michael G. Witshyn
*Assistant Examiner*—Jon P. Weber
*Attorney, Agent, or Firm*—Merchant & Gould, Smith, Edell, Welter & Schmidt

[57] ABSTRACT

Methods are presented for producing and purifying a variable fusion polypeptide which can be purified by affinity chromatography with the binding protein partner. The variable fusion polypeptide construct has tandem coupled segments containing one or more copies of a desired peptide linked to carbonic anhydrase as the purification binding protein. In the methods, the fusion protein is expressed in a recombinant host using a recombinant vector containing a gene encoding the fusion polypeptide. Then the expressed fusion polypeptide is purified by immobilized reversible inhibitor affinity chromatography. Finally, the purified fusion polypeptide is cleaved from the desired peptides by chemical or enzymatic means and the desired peptides purified with affinity chromatography.

25 Claims, 5 Drawing Sheets

OTHER PUBLICATIONS

Yoo et al. (1989) *J. Biol. Chem.*, 264(29), 17078–17083.
Amor–Gueret, et al., *Nucleic Acids Research* 18:1646 (May 1990).
Andersson, et al., *Biochemical and Biophysical Research Communications*, 48:670–677, (1972).
Asworth, et al., *Biochemical and Biophysical Research Communications*, 44:667–674 (1971).
Barlow, et al., *Nucleic Acid Research*, 15:2386, (1987).
Bergenhem, et al., *Biochimica et Biophysica Acta*, 871:55–60, (1986).
Bergenhem, et al., *Comp. Biochem. Physiol.*, 95B:205–213, (Jan. 1990).
Boyer, et al., *Annals of New York Academy of Sciences*, 429:324–331, (1984).
Brady, et al., *Biochem. Soc. Transactions*, 184–185, (1989).
Carlsson, et al., *Biochimica et Biophysica Acta*, 327:515–527 (1973).
Carter, et al., *FEBS Letters*, 128:114–118, (Jun. 1981).
Carter, et al., *Biochem. J.*, 120:797–808, (1970).
Carter, et al., *Biochem. Soc. Trans.*, 6:552–553, (1978).
Curtis, *J. Biol. Chem.*, 7:4459–4463, (Apr. 10, 1983).
Curtis, et al., *Gene*, 25:325–332, (1983).
Davis, et al., *Sematic Cell and Mol. Genet.*, 13:173–178, (1987).
Dodgson, *J. Appl. Physiol.*, 63:2134–2141, (1987).
Duff, et al., *Biochemistry*, 5:2009–2019, (1966).
Edwards, et al., *Ann. Hum. Genet.*, 50:41–47 (1986).
Edwards, et al., *Ann. Hum. Genet.*, 50:123–129 (1986).
Engberg, et al., *Archives of Biochemistry and Biophysics*, 241:628–638, (Sep. 1985).
Erikson, et al., *J. Biol. Chem.*, 261:6247–16248, (1986).
Eriksson, et al., *Proteins: Structure, Function, and Genetics*, 4:274–282, (1988).
Eriksson, et al., *Proteins: Structure, Function, and Genetics*, 4:283–293, (1988).
Feldstein, et al., *J. Biolog. Chem.*, 259:5447–5453, (1984).
Fernley, et al., *Biochem. J.*, 249:201–207, (1988).
Fernley, et al., *Biochemistry*, 27:2815–2820, (1988).
Ferrell, et al., *Biochimica et Biophysica Acta*, 533:1–11, (1978).
Fraser, et al., *J. Mol. Evol.*, 23:294–299, (1986).
Fraser, et al., *Mol. Cell. Biol.*, 9:3308–3313 (Aug. 1989).
Fridborg, et al., *J. Mol. Biol.*, 25:505–516, (1967).
Furth, *J. Biolog. Chem.*, 243:4832–4841, (1968).
Henkens, et al., *Biochemistry*, 21:5918–5923, (1982).
Henriksson, et al., *Biochem. and Biophys. Res. Comm.*, 96:135–142, (Sep. 1980).
Hewett–Emmett, et al., *Genetics*, 105:409–420, (Oct. 1983).
Hewett–Emmett, et al., *Annals New York Academy of Sciences*, 429:338–358, (1984).
Holmes, *Eur. J. Biochem.*, 78:511–520, (1977).
Holmes, *J. Exp. Zool.*, 197:289–295, (1976).
Jones, et al., *Biochimica et Biophysica Acta*, 709:284–303, (1982).
Kandel, et al., *Biochemical and Biophysical Research Communications*, 56:568–574, (1974).
Kannan, et al., *Cold Spring Harbor Symposium*, 36:221–231, (1972).
Kannan, et al., *Proc. Nat. Acad. Sci. USA*, 72:51–55, (Jan. 1975).
Kannan, et al., *FEBS Letters*, 73:115–119, (Jan. 1977).
Ko, et al., *Biochemistry*, 16(8):1720–1725, (1977).
Koester, et al., *Biochem. and Biophys. Res. Comm.*, 76:196–204, (1977).
Konialis, et al., *Proc. Natl. Acad. Sci. USA*, 82:663–667, (Feb. 1985).
Liljas, et al., *Nature New Biology*, 235:131–137, (Feb. 1972).
Lindskog, *Biochim. et Biophys. Acta*, 39:218–226, (1960).
Lloyd, et al., *Ann. Hum. Genet.*, 49:241–251, (1985).
Lloyd, et al., *Gene*, 41:233–239, (1986).
Lloyd, et al., *Genes & Development*, 1:594–602, (1987).
Maren, et al., *Ann. Rev. Pharmacol. Toxicol.*, 23:439–459, (1983).
McIntosh, *Biochem. J.*, 114:463–476, (1969).
McIntosh, *Biochem. J.*, 120:299–310, (1970).
Montgomery, et al., *Nucleic Acids Research*, 15:4687, (1987).
Murakami, et al., *Genomics I*, 159–166, (1987).
Murakami, et al., *J. Biolog. Chem.*, 262:1382–1388, (1987).
Pocker, et al., *Biochemistry*, 16:5698–5707, (Dec. 1977).
Rogers, *Eur. J. Biochem.*, 162:119–122, (1987).
Sanyal, et al., *Comp. Biochem. Physiol.*, 73B:937–944, (1982).
Shapiro, et al., *Mol. and Cell. Biol.*, 7:4589–4593, (Dec. 1987).
Stein, et al., *J. Biolog. Chem.*, 253(22):8016–8018, (Nov. 1978).
Tanis, et al., *J. Biolog. Chem.*, 245:6003–6009, (1970).
Tashian, et al., *Ann. N.Y. Acad. Sci.*, 429:49–60, 15–194, 338–358, New York, New York, (1984).
Tashian, *BioEssays* 10:186–192, (Jun. 1989).
Tilander, et al., *J. Mol. Biol.*, 12:740–760, (1965).
Venta, et al., *Biochimica et Biophysica Acta*, 826:195–201 (1985).
Venta, et al., *J. Biol. Chem.*, 260:12130–12135, (1985).
Wade, et al., *Proc. Natl. Acad. Sci. USA*, 83:9571–9575, (Dec. 1986).
Wendorff, et al., *J. Biol. Chem.*, 260:6129–6132, (1985).
Whitney, et al., *J. Biolog. Chem.*, 257:12056–12059, (1982).
Yazgan, et al., *Biochemistry*, 11(7):1314–1318, (1972).
Yoshihara, et al., *Nucleic Acids Research*, 15:753–771 (1987).
Zhu, et al., *J. Biol. Chem.*, 265:8795–8801, (May 1990).
Dicow et al. (1989) *J. Neurosci. Res.*, 22(1), 13–19.
Ford et al. (1991) *Prot. Express. Purif.*, 2(2/3), 95–107.
Greenwood et al. (1989) *FEBS Lett.*, 244(1), 127–131.
Ong et al. (1991) *Eng. Microb. Technol.*, 13, 59–65.
Germino et al. (1984) *Proc. Nat. Acad. Sci., USA*, 81, 4692–4696.
Ullmann (1984) *Gene*, 29, 27–31.
Marston (1986) *Biochem. J.*, 240, 1–12.
Smith et al. (1988) *Gene*, 67, 31–40.
Steers et al. (1971) *J. Biol. Chem.*, 246(1), 196–200.
Nilsson et al. (1985) *EMBO J.*, 4(4), 1075–1080.
Ellis et al., *Biochemistry*, 30, pp. 10806–10813 (1991).
Murray et al., *J. Biol. Chem.*, 266, pp. 11695–11698 (1991).
D. Smith et al., *Gene*, 67:3140 (1988).
R. Lerner et al., *Science*, 246, 1275 (Dec. 1989).
E. Ward et al., *Nature*, 341, 544–546 (1986).
K. Gordon et al., *Bio/Technology*, 5, 1183–1187 (1987).
C. Pittius et al., *Proc. Natl. Acad. Sci. USA*, 85, 5874–5878 (1988).
A. Clark et al., *Bio/Technology*, 7, 487–492 (1989).
Th. A. Buhler et al., *Bio/Technology*, 8, 140–143 (1990).
P. Hooykaas et al., *Methods in Enzymology*, 153, 305–313 (1987).

R. Shillito et al., *Methods in Enzymology*, 153, 313–336 (1987).
S. Cha et al., *Biochemical Pharm.*, 24, 2187–2197 (1975).
R. Agarwal et al., *Biochemical Pharm.*, 26, 354–367 (1977).
P. Taylor et al., *Biochemistry*, 9, 2638 (1970).
S. Cha et al., *Biochemical Pharm.*, 30, 1507–1515 (1981).
J. Williams et al., *Biochemical Pharm.*, 29, 589–595 (1980).
J. Pierce et al., *Biochemistry*, 19, 934–942 (1980).
W. Degrado et al., *J. of Cellular Biochem.*, 29, 83–93 (1989).
L. Sutton et al., *BBRC*, 134, 386–392 (1986).
W. Scouten, *Methods Enzymol.*, 34, 288–294 (1974).
S. Marcus, *Methods Enzymol.*, 34, 377–385 (1974).
A. Matsura et al., *Methods Enzymol.*, 34, 303–304 (1974).
R. Barker, *Methods Enzymol.*, 34, 317–328 (1974).
I. Matsumoto, *Methods Enzymol.*, 34, 329–341 (1974).
J. Johansen, *Carlsberg Res. Commun.*, 14, 73 (1976).
G. Bethell et al., *J. Biol. Chem.*, 254, 2572–2574 (1979).
A. Bradbury et al., *Biochem. & Biophys. Res. Com.*, 154, 1293–1300 (1988).
K. Ohsuye et al., *Biochem. & Biophys. Res. Com.*, 150, 1275–1281 (1988).
R. Lewis et al., *Proc. Natl. Acad. Sci. USA*, 82, 6490–6491 (1985).
H. Niall et al., *Proc. Natl. Acad. Sci. USA*, 64, 771–778 (1969).
E. Sausville et al., *J. Biol. Chem.*, 260, 10236–10241 (1985).
J. Pierce et al., *J. Biol. Chem.*, 199, 929–940 (1952).
D. Gearing et al., *Nucl. Acids Res.*, 16, 9857 (1988).
J. Rivier et al., *Nature*, 300, 276 (1982).
A. Honegger et al., *J. Biol. Chem.*, 261, 569–575 (1986).
H. Gregory et al., *Int. J. Pept. Protein Res.*, 9, 107–118 (1977).
S. Jayne et al., *BioEssays*, 6, 263–270 (1987).
S. Beaucage et al., *Tet. Letters*, 221, 859–62 (1981).
A. Rosenberg et al., *Gene*, 56, 125–135 (1987).
R. Gunsalus et al., *Proc. Natl. Acad. Sci. USA*, 79, 320–324 (1982).
R. Bird et al., *Science*, 242, 423–425 (1988).
B. Hammarberg et al., *Proc. Nat'l. Acad. Sci.*, 861, 4367–4371 (1989).
A. Hiatt et al., *Nature*, 342, 76–78 (1989).
T. Hopp et al., *Bio/Technology*, 6, 1204–1210 (1988).
G. Koppel, *Bioconjugate Chem.*, 1, 13–23 (1990).
J. Luong et al., *Bio/Technology*, 8, 306–307 (1990).
G. Pietersz, *Bioconjugate Chemistry*, 1, 89–95 (1990).
H. Sassenfeld, *TibTech*, 8, 88–93 (1990).
M. Uhlen et al., *Methods in Enzymology*, 185, 129–143 (1990).
*Gene*, 13, issued 1981, Harley et al., pp. 347–353.
*Nucleic Acids Res.*, 8, No. 20, 1980, Doel et al. pp. 4575–4592.
*Proc. Natl. Acad. Sci. USA*, 81, Aug. 1984, Shen, pp. 4627–4631.
*Tibetech*, 8, Apr. 1990, Sessenfeld, pp. 89–93.
*Genes*, 4th ed., 1990, B. Lewin, pp. 606–607.
*Cholesterol Metabolism, LDL and the LDL Receptor*, 1990, Academic Press, N. B. Myant, pp. 124–168.
*Proc. Natl. Aca. Sci. USA*, 84, 1987, B. J. Hwang et al, pp. 5550–5554.
*EMBO J.*, 2, 1983, F. Bouadloun et al., pp. 1351–1356.
*Cell*, 10, 1977, P. Edelmann et al., pp. 131–137.
*Eur. J. Biochem.*, 144, 1984, K. Khazaie et al., pp. 485–489.
Biochem. J., 128, 1972, R. B. Loftfield et al., pp. 1353–1356.
*Mol. Gen. Genet.*, 180, 1980, J. Parker et al., pp. 275–280.
*Accuracy of Molecular Processes*, Chapman and Hall, 1985, R. H. Buckingham et al., pp. 83–126.
*Annu. Rev. Biochem.*, 45, 1976, A. L. Goldberg et al., pp. 747–803.
*Annu. Rev. Biochem.*, 40, 1971, P. Cuatrecasas et al., p. 259.
*Affinity Chromatography*, 1981, William Scouten, pp. 99–102.
*Biochem. Soc. Trans.*, 1, 1973, P. O'Carra et al., p. 289.
*Methods Enzymol.*, 34, 1974, P. O'Carra et al., pp. 118–119.
*Carlsberg Res. Commun.*, 41, 1976, J. T. Johansen, pp. 73–80.

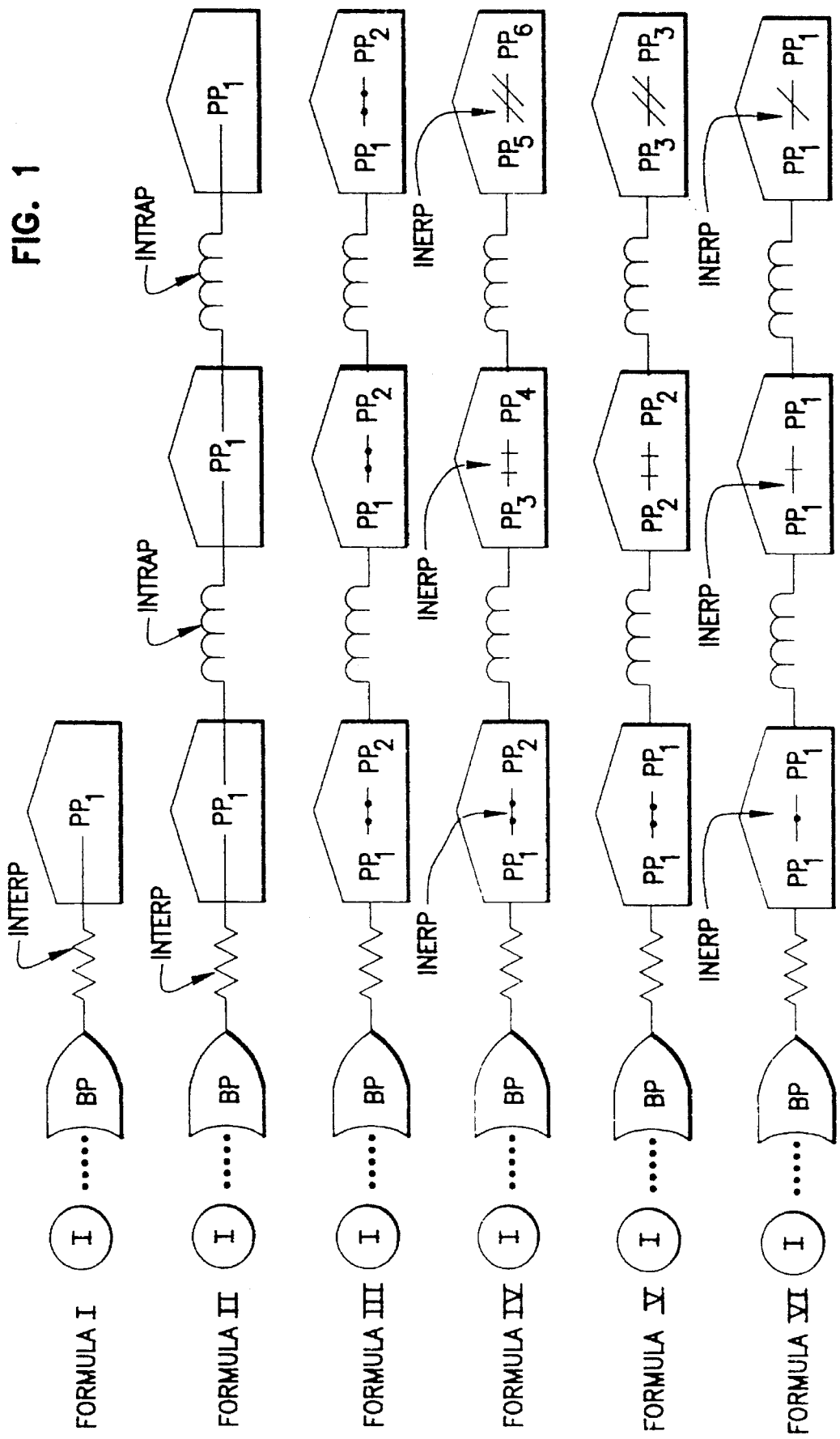

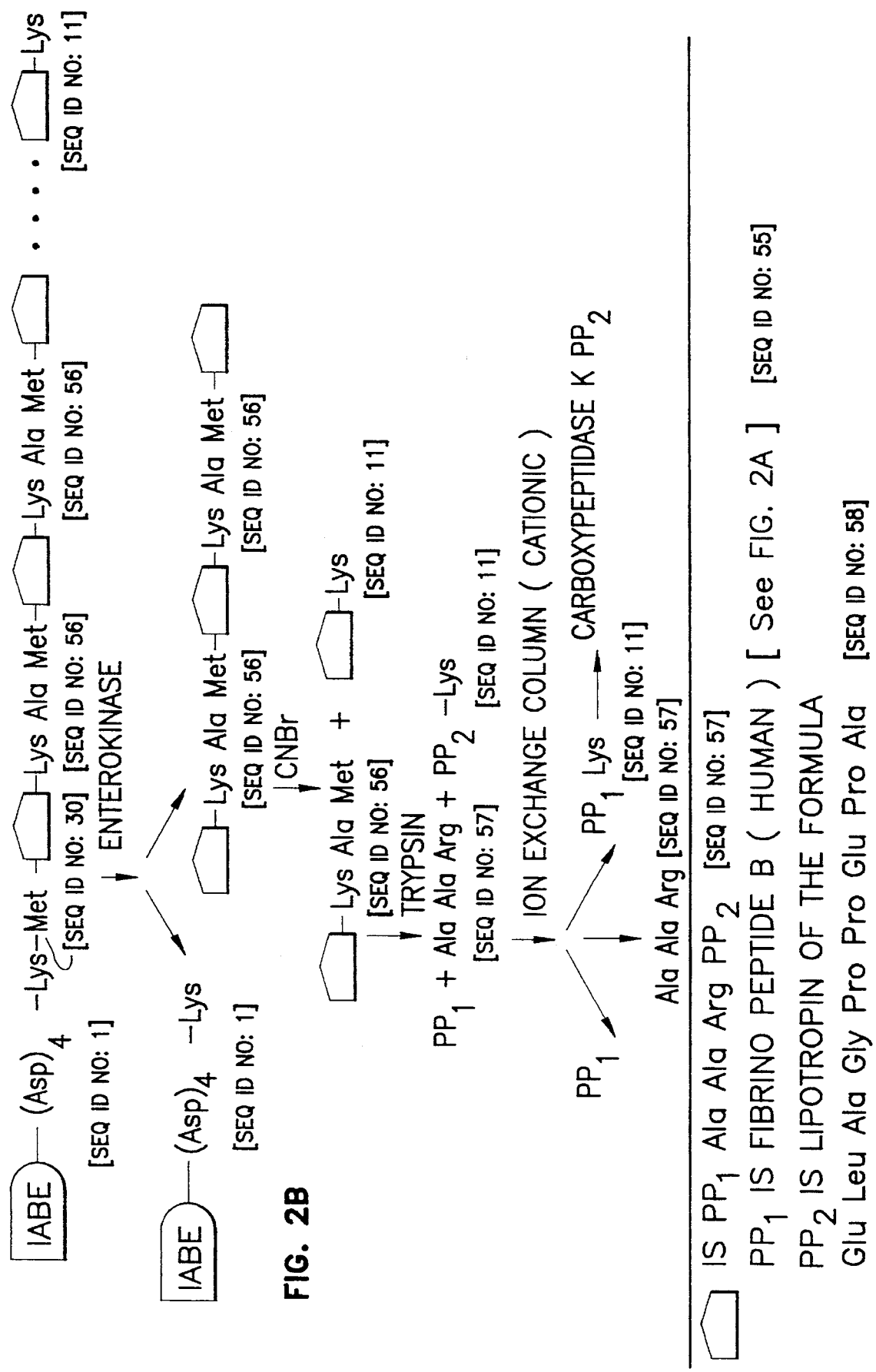

FIG. 3    CARBONIC ANHYDRASE SEQUENCE  [SEQ ID NO: 62]

```
                                            MetSerHisHisTrpGlyTyrGlyLysHisAsn
                                            ATGTCCCATCACTGGGGGTACGGCAAACACAAC
                                            1                  20
GlyProGluHisTrpHisLysAspPheProIleAlaLysGlyGluArgGlnSerProValAspIleAspThrHis
GGACCTGAGCACTGGCATAAGGACTTCCCCATTGCCAAGGGAGAGCGCCAGTCCCCTGTTGACATCGACACTCAT
    40              60              80              100
ThrAlaLysTyrAspProSerLeuLysProLeuSerValSerTyrAspGlnAlaThrSerLeuArgIleLeuAsn
ACAGCCAAGTATGACCCTTCCCTGAAGCCCCTGTCTGTTTCCTATGATCAAGCAACTTCCCTGAGGATCCTCAAC
        120             140          Sau3AI          BamHI
AsnGlyHisAlaPheAsnValGluPheAspAspSerGlnAspLysAlaValLeuLysGlyGlyProLeuAspGly
AATGGTCATGCTTTCAACGTGGAGTTTGATGACTCTCAGGACAAAGCAGTGCTCAAGGGAGGACCCCTGGATGGC
            200             220             240
ThrTyrArgLeuIleGlnPheHisPheHisTrpGlySerLeuAspGlyGlnGlySerGluHisThrValAspLys
ACTTACAGATTGATTCAGTTTCACTTTCACTGGGGTTCACTTGATGGACAAGGTTCAGAGCATACTGTGGATAAA
                280             300             320
LysLysTyrAlaAlaGluLeuHisLeuValHisTrpAsnThrLysTyrGlyAspPheGlyLysAlaValGlnGln
AAGAAATATGCTGCAGAACTTCACTTGGTTCACTGGAACACCAAATATGGGGATTTTGGGAAAGCTGTGCAGCAA
        340   PstI    360             380             400
ProAspGlyLeuAlaValLeuGlyIlePheLeuLysValGlySerAlaLysProGlyLeuGlnLysValValAsp
CCTGATGGACTGGCCGTTCTAGGTATTTTTTTGAAGGTTGGCAGCGCTAAACCGGGCCTTCAGAAAGTTGTTGAT
            420             440             460             480
ValLeuAspSerIleLysThrLysGlyLysSerAlaAspPheThrAsnPheAspProArgGlyLeuLeuProGlu
GTGCTGGATTCCATTAAAAACAAAGGGCAAGAGTGCTGACTTCACTAACTTCGATCCTCGTGGCCTCCTTCCTGAA
            500             520           Sau3AI
SerLeuAspTyrTrpThrTyrProGlySerLeuThrThrProProLeuLeuGluCysValThrTrpIleValLeu
TCCTTGGATTACTGGACCTACCCAGGCTCACTGACCACCCCTCCTCTTCTGGAATGTGTGACCTGGATTGTGCTC
            580             600             620
LysGluProIleSerValSerSerGluGlnValLeuLysPheArgLysLeuAsnPheAsnGlyGluGlyGluPro
AAGGAACCCATCAGCGTCAGCAGCGAGCAGGTGTTGAAATTCCGTAAACTTAACTTCAATGGGGAGGGTGAACCC
            640             660             680             700
GluGluLeuMetValAspAsnTrpArgProAlaGlnProLeuLysAsnArgGlnIleLysAlaSerPheLys
GAAGAACTGATGGTGGACAACTGGCGCCCAGCTCAGCCACTGAAGAACAGGCAAATCAAAGCTTCCTTCAAA
        720             740             760     HindIII    780
```

NUCLEOTIDE SEQUENCE AND DEDUCED AMINO ACID SEQUENC OF
HUMAN CARBONIC ANHYDRASE II cDNA. THE SEQUENCE IS
TAKEN FROM PETERSON AND LUND, ACTA CHEMICA SCAND., B42, 319-323 (1988)

PURIFICATION DIRECTED CLONING OF PEPTIDES USING CARBONIC ANHYDRASE AS THE AFFINITY BINDING SEGMENT

BACKGROUND OF THE INVENTION

In vitro DNA manipulation and the attendant transfer of genetic information have developed into a technology that allows the efficient expression of endogenous and foreign proteins in microbial hosts. Although expression of any foreign protein in any microbial host is theoretically possible, many problems limit its practice. Stability of the protein produced often limits such practice and results in a low yield. In particular, small foreign proteins and oligopeptides cannot be overproduced in most cellular hosts. While larger proteins can be produced at low or even high yield, their purification from the total cell extract often poses problems.

To address these concerns, several researchers have recently investigated the fusion of a peptide marker to the protein being expressed so that the protein can be readily recognized during purification. For example, a method such as the one described in U.S. Pat. No. 4,782,137, utilizes an antibody immobilized-immunoaffinity technique in combination with an expressed, fused protein containing a small antigenic oligopeptide marker having an "antigenic head" portion and a "linking tail" portion. The antigenic portion is a combination of hydrophilic amino acids that readily elicit antigenic response. The linking portion permits cleavage of the marker from the desired protein after the fused protein has been isolated from the cells.

Other methods involve expression and purification techniques combining the use of enzymatic markers such as glutathione transferase, beta-galactosidase and chloramphenicol acetyl transferase which bind to appropriate substrates. See D. B. Smith, et al., *Gene,* 67, 31–40 (1988); Japanese application JP62283998, Derwent Abstract No. 4733853 and EPO application 131,363. In these instances, the enzyme is fused to the desired protein, the fusion product separated by binding to an immobilized substrate and the enzyme cleaved from the desired protein by biochemical methods.

Expression of a small polypeptide in a host cell also raises the possibility that the host will assimilate the polypeptide. In instances where the recognition marker and desired protein are small, e.g. below about 60 to 80 amino acid units in length, assimilation rather than expression as an end-product usually occurs.

The efficiency of expression in the host cell can also vary depending upon the character of the protein being produced. The host may produce negligible amounts of fused peptide because the variation of the fused peptide structure can trigger a decrease in the transcriptional and/or translational efficiency. In particular, triggering is a problem with a system that uses a small oligopeptide marker.

Production of fusion proteins containing larger peptides exemplified by beta-galactosidase, glutathione transferase or chloramphenicol acetyl transferase generally creates a new set of difficulties. Purification usually is not very efficient or effective. For such large fusion proteins, the binding constants of the contained enzymes to their substrates usually are so low that purification is difficult to achieve. During purification the substrates often cleave from the column support and contaminate the separated fusion protein. Many of the enzymes are such large molecular weight proteins that the desired protein constitutes only a small fraction of the fusion protein.

Consequently, production and purification of large quantities of protein by a microbial route need to be based upon techniques that avoid or alleviate the foregoing concerns. Overproduction of the desired protein relative to other proteins produced by the host would also be advantageous. The protein used for binding also should be one that has a high affinity for a small molecule, so as to avoid the adverse complexing capacity, leakage, viral contamination and other problems associated with immunoaffinity chromatography.

Therefore, it is an object of the invention to develop an expression system that allows the large scale, high yield overproduction of both small and large polypeptides. A further object is to provide a facile, highly efficient purification scheme that has general applicability to any product polypeptide such as proteins or very small peptides. Yet another object is the development of protein expression and separation methods that utilize inexpensive materials. A further object is practice of the method with soluble affinity systems that permit stable and high yield expression of polypeptides. A particular object is the development of a separation system based upon affinity techniques employing a recombinant and expressed binding protein that has a high affinity for its ligand.

SUMMARY OF THE INVENTION

These and other objects are achieved by the present invention which is directed to microbial and higher organism methods for expression and ligand immobilized affinity purification of a product peptide. The invention is directed as well to biological compositions for expressing and purifying the product peptide. In particular the invention includes a protein purification construct incorporating the product peptide.

Generally, the biological compositions of the invention include:

(a) the expressed protein purification construct having three tandem, coupled segments composed of a binding protein, an interconnecting peptide and a variable fused polypeptide;

(b) a recombinant gene for the protein purification construct;

(c) a recombinant expression vector incorporating that recombinant gene;

(d) transformed cells or higher organisms carrying the vector;

(e) a gene for the binding protein fused to the interconnecting peptide; and (f) the binding protein fused to the interconnecting peptide.

The protein purification construct of the present invention has a three tandem segment, single chain formula. The first segment is a binding protein which exhibits strong, reversible binding to a specific small molecular weight ligand. The second segment is an interconnecting peptide which is selectively cleavable by an enzyme or chemical technique. It is typically a short chain peptide. The third segment, the variable fused polypeptide, incorporates any natural or synthetic polypeptide desired as a product, e.g., any desired protein, oligopeptide or small molecular weight peptide. In general, the variable fused polypeptide is composed of a single product peptide, or multiple units of product peptides. The product peptides are the ultimate products of desirable character to the consumer. The variable fused polypeptide can incorporate naturally assimilable amino acids as well as optional lipid, glycan and other ancillary moieties such as vitamin derived cofactors and/or metal ions.

The variable fused polypeptide has several forms. The first is a single product peptide. The second is composed of multiple tandem units of a single product peptide that are linked by an intraconnecting peptide. In this case, the intraconnecting peptide usually but not necessarily differs in structure and selectivity from the interconnecting peptide. When different, the intraconnecting peptide nevertheless has the same general function as the interconnecting peptide so that two different cleavages of an enzymatic or chemical nature will sequentially cleave the variable fused polypeptide from the binding protein and then the individual product peptides from each other. The third form is a single unit composed of several (i.e., two or more) identical or different product peptides tandemly interlinked together by innerconnecting peptides. The fourth form is composed of repeating multiple tandem units linked together by intraconnecting peptides wherein each unit contains the same series of different individual product peptides joined together by innerconnecting peptides. The fifth form is composed of a series of tandem units linked together by intraconnecting peptides wherein each unit contains several identical or different product peptides joined by innerconnecting peptides and the product peptides do not repeat from unit to unit. The sixth form is composed of identical multiple tandem units wherein each unit contains several identical product peptides joined by innerconnecting peptides.

Preferred embodiments of the product peptide which can appear as single or multiple linked units in the variable fused polypeptide include caltrin, calcitonin, insulin, tissue plasminogen activator, growth hormone, growth factors, growth hormone releasing factors, erythropoietin, interferons, interleukins, oxytocin, vasopressin, ACTH, collagen binding protein, assembled antibodies, individual heavy and light antibody chains, antibody fragments such as $F_{ab}$, $F_{(ab)_2}$, $F_c$, individual chain fragments especially such as the isolated variable regions (VH or VL) as characterized by Lerner, Science, 244, 1275 et. seq. (Dec. 1989) and epitopal regions such as those characterized by E. Ward et al., Nature, 341, 544–546 (1986) wherein the antibodies, chains, fragments and regions have natural or immunogenetically developed antigenicity toward antigenic substances. Additional embodiments of the desired polypeptide include polypeptides having physiologic properties, such as sweetening peptides, mood altering polypeptides, nerve growth factors, regulatory proteins, functional hormones, enzymes, DNA polymerases, DNA modification enzymes, structural polypeptides, synthetic polypeptides, neuropeptides, polypeptides exhibiting effects upon the cardiovascular, respiratory, excretory, lymphatic, immune, blood, reproductive, cell stimulatory and physiologic functional systems, leukemia inhibitor factors, antibiotic and bacteriostatic peptides (such as cecropins, attacins, apidaecins), insecticide, herbicide and fungicide peptides as well as lysozymes.

The binding protein segment of the protein purification construct generally is an enzyme-like protein including but not limited to an enzyme or a truncated, altered or modified functional version thereof (hereinafter the modified functional version). The binding protein exhibits highly selective affinity binding to a low molecular weight ligand or a synthetic derivative thereof. The binding is strong so that, in general, the conjugation of the binding protein and ligand will exhibit a solution dissociation constant (inverse of the binding constant) of no more than about $10^{-7}$M. Generally, the ligand is a reversible inhibitor for the enzyme-like protein. Preferred embodiments of the binding protein include carbonic anhydrase derived from any source, especially mammalian or human, and a modified functional version thereof which will bind with the inhibitor, sulfanilamide or derivatives thereof. An especially preferred embodiment of the modified carbonic anhydrase enzyme is a functional version which (I) does not contain methionine, (II) has all or some glutamates replaced by another amino acid, preferably aspartate, (III) has all or some arginines replaced by another amino acid, preferably lysine, (IV) has all or some asparagines replaced by another amino acid, preferably glutamine, (V) has methionine replaced by another amino acid, preferably alanine or lysine, or (VI) has cysteine replaced by another amino acid, preferably serine.

Antibodies or individual chains, regions or fragments thereof, as characterized above, and other proteins, which will strongly, biospecifically and reversibly bind to a low molecular weight ligand, can perform the same function in the same way to reach the same result as the enzyme-like protein in the context of the protein purification construct, and consequently are included within the invention as binding proteins. For antibodies or the corresponding chains, regions or fragments, the ligand is a low molecular weight antigen, preferably an aromatic moiety such as dinitrophenol.

The choice of the interconnecting peptide for the protein purification construct depends upon the choice of cleavage enzyme and product peptide sequence. In general, this interconnecting peptide sequence constitutes any peptide sequence that uniquely reacts with a highly specific cleavage enzyme or by a highly specific chemical reagent cleavage.

The recombinant gene coding for the protein purification construct incorporates three DNA segments coding for the peptide sequences of the three segments of the construct. The segments are arranged so that either the binding protein gene fragment or the variable fused polypeptide gene fragment can be read first. It is preferred to construct the protein purification construct gene so that the binding protein gene fragment is read first. The gene segments may be synthetic or derived from natural sources.

The DNA sequence or sequences for the product peptide or peptides incorporates cDNA or genomic clones isolated from their native sources as well as synthetic DNA sequences.

The expression vector containing the recombinant gene is capable of directing expression of the protein purification construct in prokaryotic or eukaryotic cells. The expression vector incorporates the protein purification construct gene and base vector segments such as the appropriate regulatory DNA sequences for transcription, translation, phenotyping, temporal or other control of expression, RNA binding and post-expression manipulation of the expressed product. The expression vector generally will include structural features such as a promoter, an operator, a regulatory sequence and a transcription termination signal. The expression vector can be synthesized from any base vector that is compatible with the host cell or higher organism and will provide the foregoing features. The regulatory sequences of the expression vector will be specifically compatible or adapted in some fashion to be compatible with prokaryotic or eukaryotic host cells or higher organisms. Post-expression regulatory sequences, which cause secretion of the protein purification construct can be included in the eukaryotic expression vector. It is especially preferred that the expression vector exhibit a stimulatory effect upon the host cell or higher organism such that the protein purification construct is overproduced relative to the usual biosynthetic expression of the host.

Transformed prokaryotic or eukaryotic cells or higher organisms carrying the appropriate recombinant prokaryotic or eukaryotic vectors constitute the transformed microbes or higher organisms of this invention. The prokaryotic cells useful as hosts include any that are amenable to expression of foreign protein. Preferred embodiments include *E. coli* and *B. subtilis*. The eukaryotic cells include unicellular organisms, such as yeast cells, as well as immortal cells from higher organisms, such as plant, insect or mammalian cells. Preferred eukaryotic cells include *S. cerevisiae, Spodoptera frupiperda*, and corn, tobacco or soybean plant cells. The higher organisms useful as hosts include higher order plants and animals having germ cells that are amenable to transformation. Included are plants such as tobacco, corn, soybean and fruit bearing plants, and invertebrate and vertebrate animals such as fish, birds and mammals especially including sheep, goats, cows, horses and pigs.

The invention as well includes a cultured, transformed cell colony or transformed plants or animals that are capable of expressing the protein purification construct.

Generally, the method of the invention calls for:

(a) host cell or host organism expression regulated by the recombinant expression vector carrying the recombinant gene coding for the protein purification construct;

(b) purification of the protein purification construct by a ligand immobilized affinity separation technique; and (c) enzymatic or chemical cleavage of the protein purification construct in one or more stages to produce the product peptide.

The expression steps of the method according to the present invention are based upon microbial or higher organism protein expression. The steps call for inserting the recombinant gene into an appropriate base vector, transforming host cells or higher organisms with the resulting recombinant vector and expressing the protein purification construct preferably as a soluble product within the host cell or higher organism, as a product that is insoluble in the cell cytoplasm, or as a secreted product by the host cell or higher organism. When higher organisms are chosen as the host, fertilized germ cells of that organism are transformed and the transformed organism grown through usual maturation techniques.

The purification steps of the method call for affinity binding of the protein purification construct to immobilized ligand, and separating it from other cellular constituents, debris and culture medium. The variable fused polypeptide is obtained from the immobilized protein purification construct through enzymatic or chemical cleavage action upon the interconnecting peptide, and separating the variable fused polypeptide from the cleavage enzyme or other material. (Throughout this application, mention of enzymatic or chemical cleavage alone will be understood to include both.)

Alternatively, the purification steps can separate the entire protein purification construct from the immobilized ligand after purification and cleave it with an immobilized cleavage enzyme or chemical reagent to produce a mixture containing the variable fused polypeptide and binding protein. This mixture can be separated by use of an immobilized ligand for the binding protein and removal of the purified, variable fused polypeptide.

When the variable fused polypeptide is a single product peptide, the foregoing separation completes the synthesis. When the variable fused polypeptide contains multiple units or a single unit of several identical or different product peptides as explained above, subsequent, sequential enzymatic or chemical cleavage of the intraconnecting peptides, and of the innerconnecting peptides, produces the product peptides in separated form.

Generally, three peptide or amino acid linkers—interconnecting linker, intraconnecting linker and innerconnecting linker—are chosen to be cleavable with different enzymes or chemicals. The combination of amino acid sequences in the binding protein and in these linkers are also chosen so that they do not duplicate amino acid sequences in the product peptides. The modifications of the binding protein mentioned above facilitate this choice.

Preferred embodiments of the method include those expressing the recombinant gene composed of DNA segments for human carbonic anhydrase (or a modified functional version thereof), interconnecting peptide and a single product peptide or multiple units thereof. Additional preferred embodiments include use of *E. coli* or yeast as the host cells and use of controlled expression by means of any induction system such as temperature, nutrients, isopropyl thiogalactoside, indole acrylic acid, carbon sources and the like, so as to allow the production of a protein purification construct that would be toxic to the host. Further preferred embodiments include use of an expression vector system for prokaryotic cells which incorporates a two plastoid construction, and an expression vector system for yeast cells which incorporates a shuttle vector with an origin of replication for *E. coli* and one for *S. cerevisiae*.

An especially preferred method involves expression of multiple tandem units of a single product peptide from a single recombinant gene carrying multiples of the DNA sequence for the product peptide.

BRIEF DESCRIPTION OF THE DRAWINGS

FIG. 1 shows the various formulas for the variable fused polypeptides formed of multiple units of product peptides.

FIGS. 2A–2C shows several specific examples based upon some of the formulas of FIG. 1.

FIG. 3 shows the amino acid sequence for a preferred binding protein, human carbonic anhydrase.

DETAILED DESCRIPTION OF THE INVENTION

Figure 2A:
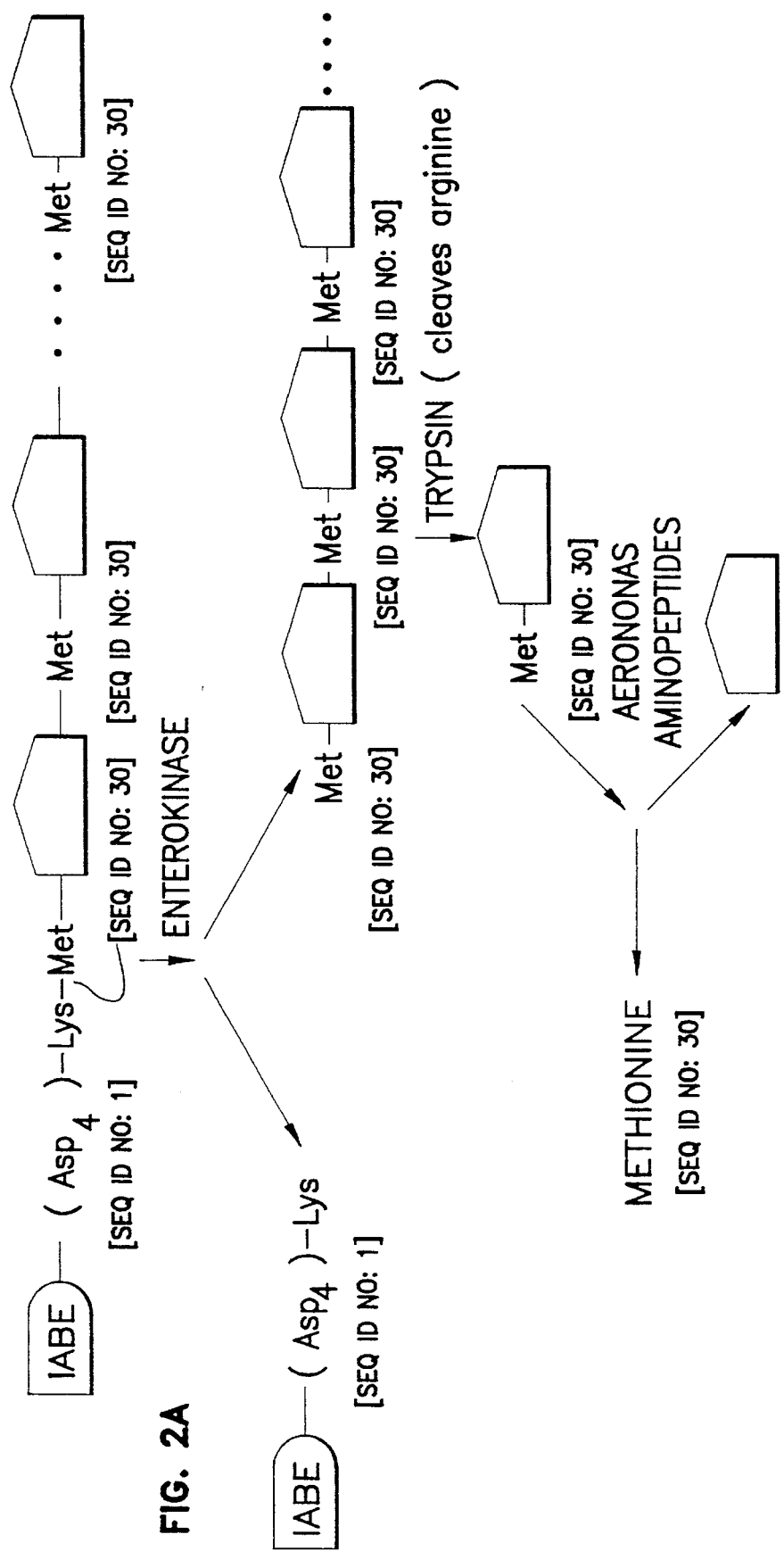

The expression of a foreign protein by interaction of recombinant vectors with the biosynthetic machinery of host cells or host organisms is a well-known technique for biochemical protein synthesis. The present invention utilizes a novel modification of this expression technique in combination with a ligand immobilized affinity separation technique to establish a new and unparalleled method for large scale, low cost, highly efficient biological synthesis. It eliminates expensive machinery and reagents, long synthetic times, low reaction efficiency and produces fewer faulty copies and a higher yield of the product peptide, than tie solid phase peptide synthesis.

The method of the invention incorporates a combination of cellular factors and biologic compositions that enable ready expression of foreign proteins by biological systems. Because the expressed protein purification construct incorporates a large binding protein, subversion of the particular identity of the product peptide by the expression mechanism of the cell or organism is not permitted. Variation in expression efficiency is minimized. The preferred inductive expression mechanism allows production of peptide purification constructs that would otherwise be toxic to host cells.

The method of the invention also incorporates factors that contribute substantially to the efficiency, capacity and yield of the purification technique. The high binding constant (low dissociation constant) of the binding protein for its immobilized ligand enables clean, complete separation of the variable fused polypeptide from other constituents. The low molecular weight of the immobilized ligand achieves a high capacity and large scale of separation per unit weight of immobilization support. When the binding protein and ligand are an enzyme and inhibitor, there is no spurious enzymatic cleavage action to produce undesirable side products.

Additional features of the invention that are advantageous include the use of the multiple unit concept and codon diversity in the gene segment for the variable fused polypeptide. Thence features are based upon the discovery that repetitious gene sequences can be unstable in the host cell.

IA. Method for Expression—Host Cells

The microbial method of the invention employs host cells transformed with an expression vector carrying a recombinant protein purification construct gene which will cause the host cells to express the protein purification construct. The vector carrying the protein purification construct gene is prepared by insertion of the DNA segments coding for the protein purification construct into an appropriate base vector.

In one scheme for construction of the vector, the DNA segment for the binding protein, for example the human gene for carbonic anhydrase II, (the binding protein gene) is inserted into a base plasmid which is compatible with the host cell to be transformed. The base plasmid contains the necessary regulatory sequences for high level expression of genes placed downstream.

A synthetic DNA sequence coding for the interconnecting peptide is then inserted near the 3' end of the binding protein gene. A restriction enzyme site near the 3' end of the bindin, protein gene should be present to enable insertion of this DNA sequence for the interconnecting peptide. Also, at least one convenient restriction enzyme site (intermediate vector restriction site) should be designed into the synthetic DNA sequence for the interconnecting peptide so that DNA segments coding for the variable fused polypeptide can later be inserted in the correct reading frame. If no such sites are already present, they can be introduced at this point in the scheme by a site-specific mutagenesis after standard procedures described in Sambrook, J., Fritsch, E. F. and Maniatis, T., *Molecular Cloning, A Laboratory Manual,* Cold Spring Harbor Laboratory, Cold Spring Harbor, N.Y. (1989), the disclosure of which is incorporated herein by reference.

The resulting vector construct is the intermediate base vector for the in site construction of the protein purification construct gene integrated into the larger vector. Any naturally occurring or synthetic DNA sequence can be inserted into the intermediate vector restriction site to yield a protein purification construct gene integrated into the expression vector. Proper insertion and reading frame alignment can be verified by known techniques such as sequencing the junction region between the binding protein gene and the DNA sequence for the variable fused polypeptide according to methods described in Sambrook et al.

Alternate synthetic routes also will provide the same construction of the final expression vector. In one alternative route, any two adjacent DNA segments of the protein purification construct gene can be ligated together to form an intermediate gene and then combined with the third segment to form the protein purification construct gene in non-integrated form (i.e., separate entity). The non-integrated protein purification construct gene can then be inserted into an appropriate base vector following the restriction and ligation methods described above. Appropriate unique restriction sites can be inserted as described above (Sambrook protocols) if not already present in the base vector chosen.

In a second alternative, after ligating together any two adjacent DNA segments, the resulting intermediate gene can be transferred to the base vector by the restriction and ligation methods described above. The third DNA segment (i.e., the binding protein gene or variable fused polypeptide gene) can be inserted into the base vector carrying the intermediate gene pursuant to the Sambrook techniques including construction of appropriate restriction sites, if needed, and ligation procedures described above.

This same methodology for final expression vector construction can be employed in the preparation of vectors carrying protein purification construct genes reading for protein purification constructs of a reverse sequence, i.e., reading as variable fused peptide-interconnecting peptide-binding protein. In this instance, the gene for the interconnecting peptide and/or other appropriate genes are inserted at the 5' end of the binding protein gene and/or other appropriate gene. All protocols for restriction, insertion, ligation and the like follow standard procedures such as those described by Sambrook, cited supra.

The final recombinant expression vector will carry an appropriate promoter, a sequence coding for a ribosome binding site, phenotype genes for selection, and regulatory regions for transcription, translation and for post-translational intracellular manipulation of the resulting protein purification construct.

Prokaryotic and eukaryotic vectors which have been constructed according to the foregoing general schemes can function or can be modified to function within the biosynthetic machinery of appropriate host cells. For eukaryotic cells, the vectors preferably can carry signal sequences and/or other regulatory sequences to allow for excellular secretion of the protein purification construct as it is expressed or allow for post-translational modifications.

Preferred base vectors for the method of invention include any plasmid that is compatible with the particular host, is stable in that host and allows for a positive selection of the transformed host. Such vectors include, for example, pTZ18/19U/R or pPL-lambda as well as those characterized in P. H. Pouwels, B. E. Enger-Valk, and W. J. Branimer, *Cloning Vectors,* Elsevier Science Pub. (1985) the disclosure of which is incorporated herein by reference.

The preferred intermediate vector restriction sites will depend on the DNA sequence of the interconnecting peptide, which in turn is dependent on the type of cleavage chosen. Any restriction enzyme site can be used which is compatible with the DNA sequence for the interconnecting peptide, or which can be manipulated by treatment with DNA modifying enzymes (such as T4 DNA polymerase, S1 nuclease, Klenow fragment, mung bean nuclease or different exonucleases) or by the addition of linkers or adapters to ensure a correct sequence and reading frame alignment in the junction region.

Isolation of host cells transformed with the final recombinant expression vector is accomplished by selecting for the phenotype or other characteristic that is designed into the recombinant vector. Generally, such selection characteristics include antibiotic resistance or complementation of deficient functions in the host. Preferred phenotype genes for the recombinant vector of the invention include antibiotic resistent phenotypes, essential amino acid phenotypes and other essential compound phenotypes.

Culturing the selected, transformed host cells in a medium containing nutrients, growth factors and vitamins will yield the protein purification construct in those cases where a non-inducible expression system is used. Preferably, an inducible expression system is used so that the selected, transformed host cell will be grown to early- to mid-logarithmic phase and treated with an induction compound to cause the protein purification construct to be produced. Typically, incubation will be continued for up to several hours (the most appropriate incubation time for each protein purification construct is determined by sampling at differing times during a test incubation), at which point the cells are harvested and lysed to release the cellular contents containing the protein purification construct. If the transformed host cell is designed to secrete the protein purification construct, the culture is grown until an appropriate and/or desired concentration of the protein purification construct is present in the culture medium. If the host cell is one that will contain dissolved protein purification construct in its cytoplasm, the culture is grown until it reaches optimum maturity. The mature culture is then lysed with an appropriate agent to release the cytoplasm containing the protein purification construct. If the protein purification construct is deposited as insoluble granules in the host cell, the mature cell culture, lysed and the released insoluble granules are dissolved in chaotropic agents and refolded in vitro. This incubation, growth and lysing process can be conducted in a batch or continuous manner.

In either alternative for producing protein purification construct, the medium containing the protein purification construct obtained from the cells is taken as a crude mixture of materials into the method for purification.

IB. Method for Expression—Higher Organisms

The multicellular method of the invention employs higher organisms transgenically altered with a genetic expression cassette carrying a recombinant protein purification construct gene which will cause the higher organism to express the protein purification construct. The cassette carrying the protein purification construct gene is prepared by insertion of the DNA segments coding for the protein purification construct into an appropriate base cassette. The base cassette will be compatible with host organism germ cells and will be designed to combine appropriately with the genetic material of those cells. It will carry or will be modified to carry the appropriate promoter, operator, regulatory and phenotype regions needed to achieve transcription, translation, and post-translation intracellular manipulation of the resulting protein purification construct.

Higher organisms, including plants such as corn, soybean and tobacco, and animals such as fish or mammals (e.g., goats, cows, horses, rabbits and mice) can function as the hosts for this method. After sexual fusion of host haploid germ cells and transformation of those fertilized germ cells with the recombinant expression cassette, the transgenic animal can be grown by reimplantation of the transgenic germ cell into the uterus and growth of the transgenic embryo. Plants also can function as the host of this method. Transgenic plants can be obtained by Agrobacterium mediated transformation, electroporation of plant protoplasts or microprojectile bombardment. Upon maturation of the transgenic plant or animal, the expressed protein purification construct can be found in the plant material, e.g., leaves, seeds, fruit, or in animal tissues, e.g., meat, organs, or in tissue secretions, e.g., sap, urine or milk. Homogenization and/or extractive concentration methods applied to the material, tissues or secretions can yield a crude mixture of materials including the protein purification construct for use in the method for purification. Generally, these methods follow the techniques and protocols described in the references in Table 1, the disclosures of which are incorporated herein by reference.

Table 1

Protocols for preparation of transgenic sheep and mice
1. Gordon K., Lee L., Vitale J. A., Smith A. E., Westphal H., and Hennighausen L. (1987) *Bio/Technology*, 5, 1183–1187.
2. Pittius C. W., Hennighausen L., Lee L., Westphal H., Nichols E., Vitale J. A., and Gordon K. (1988) *Proc. Natl. Acad. Sci. USA*, 85, 5874–5878.
3. Clark A. J., Bessos H., Bishop J. D., Brown P., Harris S., Lathe R., McLenaghan M., Prouse C., and Simons J. P. (1989) *Bio/Technology*, 7, 487–492.

Protocols for preparation of transgenic rabbits
1. Buhler Th. A., Bruyere Th., Went D. F., Stranzinger G., and Burki K. (1990) *Bio/Technology*, 8, 140–143.

Protocols for preparation of transgenic plants
1. Hooykaas P. J. J., and Schilperoort R. A. (1987) *Methods in Enzymology*, 153, 305–313.
2. Shillito R. D., and Potrykus I., (1987) *Methods in Enzymology*, 153, 313–336.
3. Weissinger A., Thomes D., Maddock S., Fromm M., and Sanford J. (1988) in *Current Communications in Molecular Biology*, (Fraley R. T., Frey N. M., and Schell J., eds.) Cold Spring Harbor, N.Y.
4. Lichtenstein C., and Draper J. (1986) in *DNA Cloning*, vol. II, (Glover D. M. ed.), IRL Press Ltd., Oxford UK.

II. Method for Purification

To perform purification, the crude mixture of materials is combined with an immobilized ligand for the binding protein. Examples of the binding protein, corresponding ligand and associated dissociation constants are given in following Table 2. For the preferred carbonic anhydrase enzyme, the ligand is sulfanilamide or a benzene sulfonamide derivative with a dissociation constant of no greater than $10^{-7}$. For preferred avidin/streptavidin the ligand is the biotin analog 2-amino biotin with a dissociation constant of on the order of biotins but which dissociate when the pH is raised and the ligand associates with a proton. The protein purification construct binds to the immobilized ligand through the reversible affinity of the binding protein for its ligand. The remaining constituents and debris of the crude mixture of materials can then be removed by washing or similar techniques.

TABLE 2

| Binding Protein | Ligand | Kd | ref. |
|---|---|---|---|
| Xanthine Oxidase | Allopurinol | strong | 1 |
| Adenosine deaminase | Coformycin | <1.2E-10 | 1 |
| Adenosine deaminase | Deoxycoformycin | 2.5E-12 | 2 |
| Adenosine deaminase | erythro-9-(2-hydroxy-3 nonyl) adenine | 1.6E-9 | 2 |
| Dihydrofolate reductase | Methotrexate | 1.2E-9 | 4 |
| Dihydrofolate reductase | Methotrexate | 2.3E-9 | 5 |
| Dihydrofolate reductase | Aminopterin | 3.7E-9 | 5 |
| Dihydrofolate reductase | Trimethoprin | 4.6E-9 | 5 |
| Ribulose bisphosphate carboxylase | 2 carboxyarabiritol 1,5 bisphosphate | 1E-14 | 6 |
| Pepsin | Pepstatin | 10E-9 | |
| Calmodulin | Melittin | 3E-9 | 7 |
| Calmodulin | Various peptides | 0.2E-9 | 7 |
| Cholesterol esterase | `Borinic acid | 0.1E-9 | 8 |
| Carbonic anhydrase II | Sulfanilamide | 4.6E-7 | 3 |
| Carbonic anhydrase II | Acetazolamide | 6 E-10 | 3 |
| Hemoglobin | Cyanide | — | — |

TABLE 2-continued

| Binding Protein | Ligand | Kd | ref. |
|---|---|---|---|
| F$_1$ ATPase | AMPPNP | — | — 5 |
| ATPase | Vanadate | — | — |

E is times ten to the negative exponent indicated.
References Cited in Table 2
1. Cha et al., Biochemical Pharm. 24, 2187–2197.
2. Agarwal et al., Biochemical Pharm., 26, 354–367 (1977).
3. Taylor, P. W. et al., Biochemistry, 9, 2638 (1970).
4. Cha et al., Biochemical Pharm., 30, 1507–1515 (1981).
5. Williams et al., Biochemical Pharm., 29, 589–595 (1980).
6. Pierce, J., Tolbert, N. E., Barker, R., Biochem., 19, 934–942 (1980).
7. Degrado et al., J. of Cellular Biochem., 29, 83–93 (1989).
8. Sutton et al., BBRC, 134, 386–392 (1986).

Immobilization of the ligand on a solid support can be accomplished by the methods of W. Scouter, *Methods Enzymol.*, 34, 288–294 (1974); S. Marcus, *Methods Enzymol.*, 34, 377–385 (1974); A. Matsura et al., *Methods Enzymol.*, 34, 303–4 (1974); R. Barker, *Methods Enzymol.*, 34, 317–328 (1974); I. Matsumoto, *Methods Enzymol.*, 34, 324–341 (1974), J. Johansen, *Carlsberg Res. Commun.*, 14, 73 (1976) and G. S. Bethell et al., *J. Biol. Chem.*, 254, 2572–2574 (1979); the disclosures of which are incorporated herein by reference. Preferred solid supports include cellulose derivatives, polyamides, dextrin, gels, polystyrene, polyolefins, silicas and glasses. Alternatively, the ligand may be coupled to an iron containing molecule such as a ferrocenyl derivative and a magnet used to perform the immobilization and separation of the iron bound protein purification construct. Liquid—liquid affinity purification can also be used. In this instance the ligand is bound to a substance that conveys selective solubility of the protein purification construct in a particular solvent system relative to the other materials present in the crude mixture.

Two routes can be employed for further purification of the protein purification construct. According to the first route, the protein purification construct is dissociated intact from the immobilized ligand by washing with a strong competing ligand solution. Examples include cyanides, pseudocyanides such as thiocyanides, perchlorates, halide and similar strong Lewis bases. According to the second route, the immobilized protein purification construct is contacted directly with cleavage reagent to release the variable fused polypeptide.

To isolate the variable fused polypeptide in the first route, the purified protein purification construct is contacted with cleavage reagent (immobilized or soluble) to cleave the protein purification construct into binding protein-interconnecting peptide moiety and the variable fused polypeptide. Contact of this mixture with the immobilized ligand for the binding protein will bind the binding protein-interconnecting peptide moiety and allow the removal of the cleaved variable fused polypeptide. If the cleavage reagent is soluble, it can be separated from the cleaved variable fused polypeptide by ordinary known techniques such as partition chromatography, dialysis, filtration based upon molecular size, high pressure liquid chromatography ion exchange chromatography and the like.

To isolate the variable fused polypeptide in the second route, its mixture with cleavage enzyme may be combined with a means for molecular weight selection (e.g. partition chromatography dialysis, filtration based on molecular size or high pressure liquid chromatography on a "particle exclusion" base or ion exchange chromatography) such that the high molecular weight cleavage enzyme is separated from the free variable fused peptide. Or, the mixture can be combined with an immobilized affinity material for the cleavage enzyme.

Depending upon the expression gene chosen, the free variable fused polypeptide released from the interconnecting peptide cleavage will constitute:

(a) the product peptide in isolated form, or (b) multiple units of product peptide(s) that need further manipulation.

Several forms of the multiple units are possible as mentioned above. In a first form, the multiple units may constitute a series of identical product peptides linked together by intraconnecting peptide fragments that differ in structure and selectivity from the interconnecting peptide already cleaved. In this form, enzymatic cleavage of the intraconnecting peptide yields free multiple copies of the product peptide. Especially when the product peptide is composed of one hundred or less amino acids this multiple unit method is an efficient way to convert a major portion of the weight of the cellular protein products into the product peptide In another form, the multiple units may be the same repeating unit of a series of different product peptides or non-repeating units composed of several identical or different product peptides. The units are linked together by the above-mentioned intraconnecting peptide while the different product peptides within the unit are linked together by innerconnecting peptides. The different product peptides are selected so that their physical or chemical properties permit their separation by conventional or affinity means. To facilitate individual product peptide separation, the intraconnecting and innerconnecting peptides serve not only as sites for peptide cleavage but also the resulting cleavage residues contribute to the chemical or physical differentiation which permits separation of individual product peptides. The ionic, lipophobic, acidic, basic or antigenic function of the intraconnecting and innerconnecting peptide residue alone or in combination with the attached product peptide permits separation of individual product peptides after cleavage by means such as affinity chromatography, ion exchange chromatography, reverse or normal phase chromatography, counter current distribution, acid or base extraction and other known methods for peptide separation. In operation, the intraconnecting and innerconnecting peptides are designed so that they may be effectively and selectively cleaved by enzymatic means and the resulting cleavage residue can be effectively and efficiently removed from the product peptide by chemical or enzymatic techniques. Typically, the intraconnecting and innerconnecting peptide cleavage residues can be removed from the product peptides by appropriate enzymatic digestion with a carboxypeptidase or aminopeptidase.

Generally, the interconnecting peptide, intraconnecting peptide and innerconnecting peptide fragments will have different amino acid sequences so that they can be sequentially rather than simultaneously cleaved. The amino acid sequences are chosen also so that the cleavage sequence does not duplicate any amino acid sequence of the product peptide(s). These three peptide connecting fragments can be chosen from the same group of amino acid unit sequences for example, those listed in following Table 3. The factors to consider in choosing these three peptide connecting fragments include the following:

a) The amino acid sequence of the product peptides. The connecting fragments cannot contain amino acid sequences that are in the product peptides.

b) Fragments with high cleavage specificity should be cleaved first while those with lower specificity should be cleaved later. This factor means that cleavage of the interconnecting peptide should be practiced according to a plan that renders this cleavage highly selective relative to the amino acid sequence of the variable fused polypeptide. Medium and low specificity can be used with the intra and innerconnecting peptide respectively. For example, methionine cleavage, which has low specificity, is most appropriately to use with the innerconnecting peptides.

c) The binding protein cannot contain readily accessible amino acid sequences that also constitute the interconnecting peptide sequence. The binding protein amino acid sequence can be modified as described above to eliminate such overlap and increase design flexibility.

d) The intra and innerconnecting peptides and the gene fragments coding for them are positioned and altered to provide for diversity in the gene sequence for the variable fused peptide. This diversity allows efficient expression of multiple units of a small peptide. It has been discovered that a continuously repetitive genetic sequence will often be rearranged or deleted by the host organism prior to recombination.

The several versions of the protein purification construct based upon the variable fused polypeptide are depicted in FIG. 1. Formula I illustrates a straightforward version of the protein purification construct as a three segment combination of the binding protein (BP), interconnecting peptide (INTERP) and product peptide (PP). Formula II illustrates a multiple unit (U) version of the protein purification construct in which the variable fused polypeptide is composed of multiple tandem units of identical PP linked together by intraconnecting peptides (INTRAP). Formula III illustrates multiple units linked together by INTRAP's, the units containing two different PP's interlinked by an innerconnecting peptide (INERP). Formula IV illustrates multiple units in which each unit is a series of three PP's interlinked by INERP's. Formula V illustrates multiple units wherein each unit in the sequence contains a different series of three identical PP's. Formula VI illustrates multiple units wherein each unit contains the same series of PP.

Figure 2C:
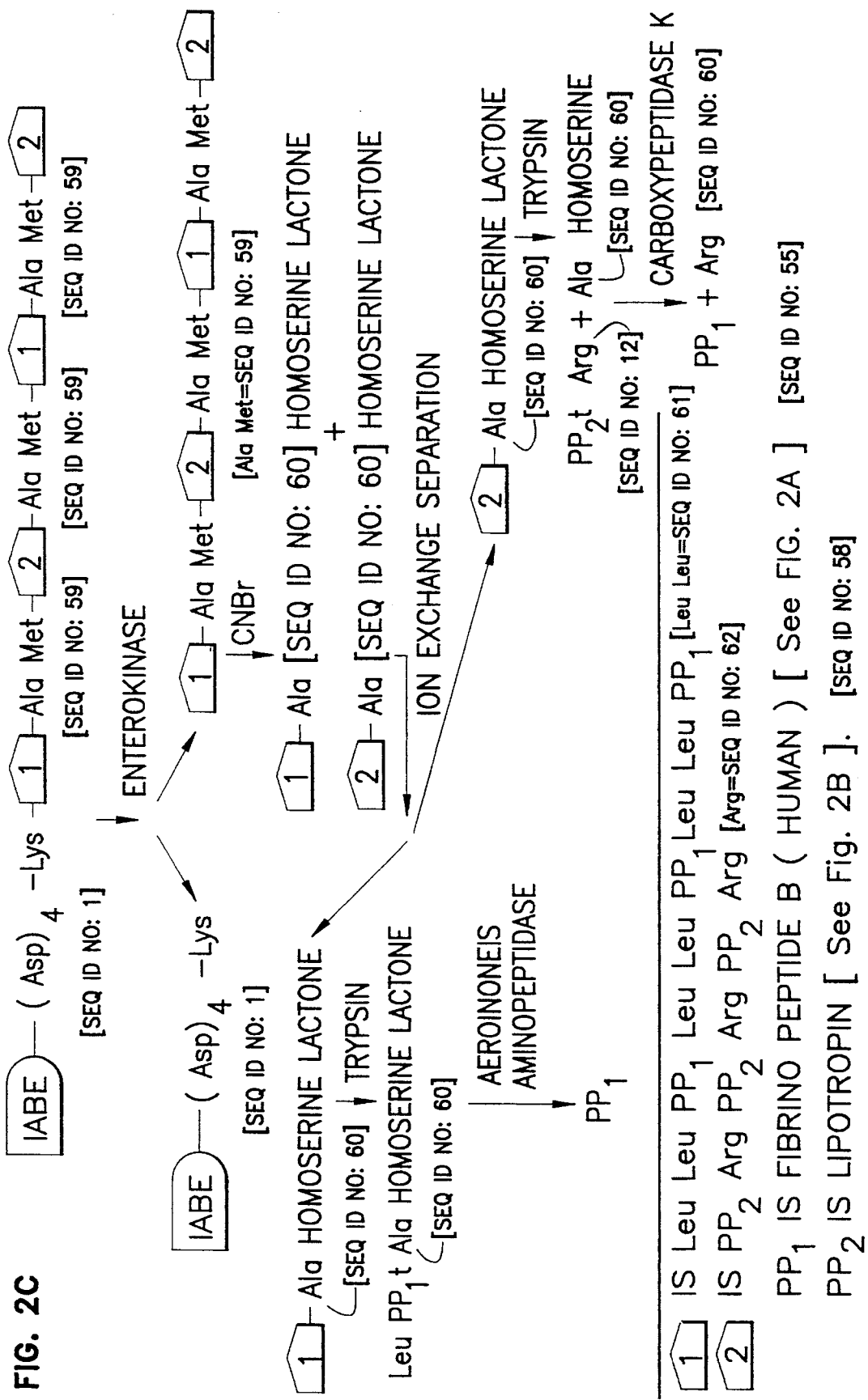

For illustrative purposes, examples of Formulas I, II, III and IV of FIG. 1 using specific product peptides are shown in FIGS. 2A–2C.

FIG. 2A is based upon Formula II of FIG. 1 and shows the structure for a protein purification construct formed from modified human carbonic anhydrase (methionine elimination) as the binding protein and multiple units of Fibrino Peptide B (human) as the variable fused polypeptide. The multiple units are linked by methionine. The variable fused polypeptide is linked to the binding protein by a tetraaspartyllysine interconnecting peptide. Selective cleavage of the connecting peptides with enterokinase (cleaves INTERP) and then with trypsin (cleaves at the carboxy side of arginine) produces N-Methionine Fibrino Peptide B.

FIG. 2B is based upon Formula III of FIG. 1 and shows the structure for a protein purification construct formed from modified human carbonic anhydrase (methionine elimination) as the binding protein and multiple units of Fibrino Protein B (human, $PP_1$) and lipotropin ($PP_2$) joined by a dialanylarginine innerconnecting peptide. The multiple units are linked by a lysinylalaninylmethionine intraconnecting peptide. The interconnecting peptide is tetraaspartyllysine. As shown sequential cleavage with enterokinase (INTERP cleavage), then cyanogen bromide (INTRAP cleavage), and then trypsin (INERP cleavage) followed by ion exchange chromatography and carboxypeptidase digestion of the connecting peptide residues produces the free Fibrino Peptide B and lipotropin.

FIG. 2C is based upon Formula V of FIG. 1 and shows the structure for a protein purification construct formed from modified human carbonic anhydrase (methionine elimination) as the binding protein and two repeating multiple units, the first being repetitious of Fibrino Protein B (human) innerconnected by dileucine and the second being repetitious of lipotropic interconnected by arginine. The multiple units are linked by alaninylmethionine intraconnecting peptide. The interconnecting peptide is tetraaspartyllysine. As shown, sequential cleavage with enterokinase (INTERP cleavage) then cyanogen bromide (INTRAP cleavage) followed by ion exchange chromatography and trypsin or aminopeptidase digestion to remove the connecting peptide residues produces the free Fibrino Peptide B and lipotropin.

When the product peptide contains an amide group instead of carboxylic acid at its C-terminus, the synthetic method of the invention can be altered and extended to produce that amide substituted protein by the addition of one or more amino acids to the c-terminus. In one embodiment of this method, the DNA code for an amino acid, e.g., glycine, can be added to the C-terminus of the gene for the product peptide. The product peptide is expressed with this additional amino acid fragment at the C-terminus. Use of the amidating enzyme described in the publications A. F. Bradbury, D. G. Smyth, *Biochem. & Biophys. Res. Com.*, 154, 1293–1300 (1988); Kazuhiro Ohsuye et al., *Biochem. & Biophys. Res. Com.*, 150, 1275–1281 (1988) will cleave the C-terminus amino acid between the N and $CH_2$ groups so as to leave a primary amide group. Other methods based upon C-terminus amino acid rearrangement and cleavage are also known and available for formation of the C-terminus amide group.

The method of the present invention circumvents the synthetic and purification difficulties of prior marker, antibody and enzyme recombinant techniques for polypeptide recombinant synthesis. For instance, the first segment of the protein purification construct is large enough to reduce any significant effects on the translational efficiency that could be caused by the variation of the sequence of the variable fused polypeptide. The use of a low molecular weight ligand and a binding protein having a strong binding constant for the ligand avoids low concentrations of the binding agent on the column and inefficient separations that are attendant with antibody and substrate-enzyme techniques. A highly leveraged binding capacity is produced for the separation as a result of the small size of the ligand relative to the large protein purification construct. The present technique also provides an inexpensive affinity ligand (inhibitor) and indefinite reuse of the purification column. Further, the method incorporating the preferred synthetic gene and expression vector allows overproduction of short peptides otherwise degraded in bacterial cells or fungi cells.

The method of the invention preferably employs a large DNA segment for the binding protein at the expression start site of the vector. With this preferred arrangement, the host cell reads the 5'-end codons of the recombinant vector as being the same in all instances even though the DNA sequence at the 3'-end of the gene can differ. With this preferred arrangement, expression is less dependent upon the variability of sequence of the gene segments for the variable fused polypeptide (product peptide), does not undergo reversion because of a repetitive product peptide sequence and relies upon the constancy of the sequence of the gene segment for the binding protein. This arrangement results in a more consistent expression system for any product peptide.

In particular, for multiple unit expression, it has been discovered that this preferred arrangement causes significant recombinant cell tolerance for the repetitive character of the variable fused protein containing more than one copy of a product peptide, and the corresponding inserted gene. Therefore, a variable fused polypeptide containing multiple units of product peptide is effectively and efficiently produced by this invention. In combination with the sequence variability provided by the multiple unit construct described above, this preferred arrangement further increases the product yield of the recombinant expression according to the invention.

The method of the invention also allows the synthesis of oligopeptides which cannot be prepared by a recombinant technique that incorporates a small antigenic peptide as an antibody separation marker. Oligopeptides with less than 50 amino acids are typically very unstable in microbes such as *E. coli* or yeast. The addition of an antigenic peptide marker containing, for example, eight amino acid units will not alter the instability. Hence, oligopeptide biosynthesis, which, for example, would include the biosynthesis of calcitonin, proinsulin, vasopressin, angiotensin, caltrin, LHRH, growth hormone releasing factor, cecropins, apidaecins and the like, cannot be accomplished through application of such a technique.

The method of the invention also avoids the difficulties attendant to techniques for expressing large proteins fused to short peptide markers. In these instances, the large proteins can fold back and block the short peptide marker. The marker would then be unavailable for complexation with, for example, an immobilized antibody. Also, use of a short leader peptide marker can cause variations in the overall expression efficiency, because the translational efficiency will become dependent on the DNA sequence of the large protein.

The method of the invention further employs a biospecific, ligand-binding protein affinity purification that separates large volumes of highly concentrated protein purification construct. This has a distinct advantage over antibody immobilized affinity chromatography methods where the size and molecular weight of the antibody are limiting factors for the amount of antigenic material (e.g. expressed protein) that can be complexed with a given unit weight of immobilized antibody and a given unit volume of affinity resin. In addition, the method of the invention avoids antibody leakage, microbial and viral contamination and other problems associated with immunoaffinity chromatography.

The binding of ligand to binding protein according to the invention is highly specific so that there is significant discrimination against undesired side products. The binding strength of this conjugate is quite high, on the order of approximately $10^{-7}$M or less as measured by its inverse function, the dissociation constant. This strength means that non-specific binding of undesired side products can be eliminated by treatment with a mild debinding agent in contrast with what would happen with systems of lower binding strengths. Because the binding constant operating in the present invention is high, relatively powerful washing and/or dissolution systems can be adapted to the purification technique. For example, washing with 1M aqueous solution of a mineral acid salt of a metallic ion, will not dissociate the binding protein-ligand couple on the support matrix in all instances according to the invention. Because the ligand-binding protein couple occupies a small volume relative to antibody-antigen volumes, however, an extremely high separation capacity per unit volume of immobilizing medium is possible.

When the ligand and binding protein couple is the especially preferred embodiment, inhibitor-enzyme, its use, rather than a substrate-enzyme conjugate permits achievement of a high binding strength rivaling that of the antibody-antigen affinity. Moreover, lack of a substrate conjugate negates the drawback of substrate based systems wherein the substrate can undergo reaction upon enzyme conjugation.

III. Preferred Embodiments

According to the present invention, a synthetic or cDNA gene coding for the product peptide and a DNA sequence for the interconnecting peptide are cloned directly adjacent to the hCAII gene presented in a recombinant vector. The resulting recombinant expression system preferably allows overproduction of the protein purification construct. The protein purification construct can then be purified through the inhibitor affinity function of the hCAII moiety.

Generally, any product peptide can be overproduced and purified by the method of the invention. The method is especially useful for overproduction of oligopeptides, which would be unstable in a "non-fused" form in the cellular host.

Specific embodiments for practice of the invention according to the preferred method employing carbonic anhydrase as the binding protein will further illustrate the advantages of the present invention. The illustrated combinations and compositions for practice of the method are based upon human carbonic anhydrase II. Additional embodiments of the ligand and binding protein included within the invention:

a) dinitrophenol as the ligand and the $F_{ab}$ of the corresponding immunospecific monoclonal antibody;

b) succinate as the ligand and carboxypeptidase Y (preferred); and c) p-aminobenzoyl glutamate and carboxypeptidase G (preferred).

III. A. Biological Compositions

1. DNA and Amino Acid Sequences for Protein Purification Construct a. Binding Protein Segment The DNA and amino acid sequence for the especially preferred carbonic anhydrase binding protein, human carbonic anhydrase II (hCAII), is given in FIG. 3. When employing the hcAII gene, at least a portion representing the functional fragment of the enzyme, such as but not limited to carbonic anhydrase terminated at methionine 239, cysteine 205 or asparagine 231 and carbonic anhydrase modified as follows:

i. hCAII with all or some glutamate amino acid residues replaced by a different amino acid (AA), preferably aspartate.

ii. hCAII with all or some arginine AA residues replaced by a different AA, preferably lysine.

iii. hCAII with the AA positions at [N11X, G12X] (asparagine glycine), [N62X, G623X], [N231X, G232X], M240X (methionine), or C205X (cysteine) modified as follows: the asparagine is changed to glutamine or glycine is changed to alanine, methionine is changed to alanine or leucine, and cysteine is changed to serine, or a combination of any of these.

In particular, the complete hCA gene sequence can be inserted into an expression vector which is compatible with *E. coli*. Cleavage of the DNA sequence at a site downstream from the regulatory portion of the vector followed by insertion of the gene through blunt- or sticky-end ligation forms the recombinant vector. Additionally, an optional restriction site sequence at the 5' or 3' end of the enzyme gene can be introduced so that subsequent manipulation can be made.

III. A.1. b. Inter- Inner- and Intraconnecting Peptide Segments

A short DNA fragment coding for the interconnecting peptide is inserted near the 3' or 5' end of the intact or partial hCA gene (the inner- and intraconnecting peptides are discussed below). This fragment can be inserted before or after the hCA gene or fragment has been transferred to the expression vector. The accuracy of the reading frame can be ensured since the nucleotide sequence of the hCA gene is exactly known. Upon insertion, however, the DNA sequence in the junction region is verified using standard DNA sequencing methods described in Sambrook et al., cited supra.

Several DNA and peptide sequences for the inter-, inner- and intraconnecting peptides and their corresponding cleavage enzymes or chemical cleavage conditions are possible. The preferred sequences and enzymes are given in following Table 3. The gene sequence indicated is one possibility coding for the inter-, inner- and intraconnecting peptides. Other DNA sequences can be constructed to code for the same inter-, inner- or intraconnecting peptide sequence.

TABLE 3

| Enzymes for Cleavage | Inter-, Inner- or Intraconnecting Linker | DNA Seq. |
|---|---|---|
| Enterokinase | (Asp)$_4$Lys | GACGACGACGATAAA |
| Factor Xa | IleGluGlyArg | ATTGAAGGAAGA |
| Thrombin | ArgGlyProArg | AGAGGACCAAGA |
| Ubiquitin Cleaving Enzyme | ArgGlyGly | AGAGGAGGA |
| Renin | HisProPheHisLeu—LeuValTyr | CATCCTTTTCATC-TGCTGGTTTAT |
| Trypsin | Lys or Arg | AAA OR CGT |
| Chymotrypsin | Phe or Tyr or Trp | TTT or TAT or TGG |
| Clostripain | Arg | CGT |
| S. aureus V8 | Glu | GAA |

| Chemical Cleavage | Inter-, Inner- or Intraconnecting Linker | DNA Seq. |
|---|---|---|
| (at pH3) | AspGly or AspPro | GATGGA |
| (Hydroxyl-amine) | AsnGly | AATCCA |
| (CNBr) | Methionine | ATG |
| BNPS-skatole | Trp | TGG |
| 2-Nitro-5-thiocyano-benzoate | Cys | TGT |

III. A.1 c. Variable Fused Peptide Segment

The third part of the sequence consists of a DNA sequence coding for the variable fused polypeptide which in a preferred embodiment is a single product peptide or multiple units of product peptide. The unit can in turn contain one or two product peptides. To form the single product peptide, the single copy gene is ligated to a DNA segment for an interconnecting peptide selected from the foregoing list. To form the double product peptide incorporated into multiple units, the combination of DNA sequences for the two product peptides, which are linked together by a DNA sequence for the innerconnecting peptide, is linked to a DNA sequence for an intraconnecting peptide selected from the foregoing list. Through repetitive cloning, multiple units of the gene can be combined together. This multiple unit gene then constitutes the code for variable fused peptide segment.

In addition to polypeptides formed from amino acid units alone, polypeptides that undergo post-translational modification may also be produced by the method of the present invention. Examples include glycoproteins, lipoproteins, N-terminal acetylated proteins, and the like which can be produced by host cells that naturally accomplish such post-translational modifications. Polypeptides containing amino acids that cannot be handled by cellular biosynthetic pathways, e.g. D-amino acids and synthetic amino acids, usually cannot be produced by the method of this invention unless specific genetic alteration of the cellular system is made to account for them.

Preferred single copy or multiple unit embodiments of the variable fused polypeptide include the sequences for the preferred embodiments of product peptides mentioned in the general section above. The peptide sequences for some of these polypeptides are known as indicated in Table 4. The disclosures of the references cited in Table 4 are incorporated herein by reference.

Table 4

Peptide Sequences

1. Caltrin:

Lewis, R. V., San Agustin, J., Kruggel, W., and Lardy, H. A. (1985) *Proc. Natl. Acad. Sci. USA* 82, 6490–6491;

2. Calcitonin (3 sequences):

Niall, H. D., Keutmann, H. T., Copp, D. H., and Potts, J. T. Jr., (1969) *Proc. Natl. Acad. Sci. USA* 64, 771–778; Keutmann, H. T., Lequin, R. M., Habener, J. F., Singer, F. R., Niall, H. D., and Potts, J. T. Jr., (1971) *Endocrinology, Proceedings of the Third International Symposium,* Taylor, S., ed., p. 316–323, Heinemann Medical Books, London;

3. Vasopressin:

Sausville, E., Carney, D., and Battery, J. (1985) *J. Biol. Chem.* 260, 10236–10241;

4. Oxytocin:

Pierce, J. G., Gordon, S., and du Vigneaud, V. (1952) *J. Biol. Chem.* 199, 929–940;

5. Leukemia Inhibitor factor: Gearing, D. P., King, J. A., and Gough, N. M. (1988) *Nucl. Acids Res.* 16, 9857;

6. LH-RH has the following sequence:

Glu His Trp Ser Tyr Gly Leu Arg Pro Gly; See Metzler D. E. in *Biochemistry* (1977), Academic Press, London.

7. ACTH (adrenocorticotropin, human) has the following sequence:

Ser Tyr Ser Met Glu His Phe Arg Trp Gly Lys Pro Val Gly Lys Lys Arg Arg Pro Val Lys Val Tyr Pro Asn Gly Ala Glu Asp Glu Ser Ala Glu Ala Phe Pro Leu Glu Phe; See Metzler D.E. in *Biochemistry* (1977), Academic Press, London.

8. Growth hormone release factor:

TryAlaAspAlaIlePheThrAsnSerTyrArgLysValLeuGly GlnLeuSerAlaArgLysLeuLeuGl- nAspIleMetSerArgGlnGln GlyGluSerAsnGlnGluArg- GlyAlaArgAlaArgLeu-NH2 (J. River et al., *Nature*, 300, 276 (1982).

9. Insulin-like Growth Factor I (IGFI) (bovine).

10. Insulin-like Growth Factor II (bovine):

Honegger, A., and Humbel, R. E. (1986 *J. Biol. Chem.* 261, 569–575;

11. Epidermal Growth Factor (Urogastrone):

Gregory, H., and Preston, B. M. (1977) *Int. J. Pept. Protein Res.* 9, 107–118;

12. Cecropins Attacins:

Jayne, S. J. M., Xanthopoulos, K. G., Destefano-Beltran, L., and Dodds, J. H., (1987) *BioEssays* 6, 2630270;

13. Angiotensin II:

Asp Arg Val Tyr Ile His Pro Phe; See Metzler D. E. in *Biochemistry* (1977), Academic Press, London.

14. Substance P:

Arg Pro Lys Pro Gln Gln Phe Phe Gly Leu Met; See Alberts B., Bray D., Lewis J., Raff M., Roberts K., and Watson J. D. in *Molecular Biology of the Cell*, 2nd ed. (1989).

15. Cholecystokinin-8:

Asp Tyr Met Gly Trp Met Asp Phe; See Alberts B., Bray D., Lewis J., Raff M., Roberts K., Watson J. D. in *Molecular Biology of the Cell*, 2nd ed. (1989).

III. A. 2. Expression Vector Incorporating Recombinant Gene

The final recombinant expression vector incorporating the protein purification construct gene is compatible with the host cell. The vectors used will have many features in common. These features include an origin of replication compatible with the host cell, regulatory DNA sequences for transcription and regulation of transcription (for inducible systems), an efficient ribosomal binding site (for prokaryotic hosts), a poly-A signal (for eukaryotic hosts). In addition, phenotype genes, regulatory regions and leader sequences can be included.

The prokaryotic vectors such as those for expression in *Escherichia coli* are characterized by an origin of replication, a genetic marker (phenotype) for selection of transformed bacteria, and DNA regulation sequences that will direct the expression of the gene of interest. The regulation sequences typically will include a promoter (P) to drive the transcription, an operator (O) to control transcription (on/off switch), an efficient ribosome binding site (RBS) to start translation, and a transcription termination signal. The start and stop codons are provided by the inserted (protein purification construct) gene.

The prokaryotic vector in particular contains a suitable "expression cassette" which is based upon any of the available promoter/operator systems. Typical promoters for inclusion in the prokaryotic vector include lactose, tryptophan, T7, lipoprotein, alkaline phosphatase, lambda leftward or rightward promoter or a combination of these (hybrid promoters). The lactose and tryptophan operators, as well as temperature sensitive lambda promoters are typical on/off switches that can be included in the prokaryotic vector. Typical phenotypic markers for inclusion in the prokaryotic vector include genes for development of resistance to ampicillin, tetracycline, kanamycin, chloramphenicol.

The preferred two-plasmid prokaryotic system contains the T7 promoter to drive the expression of the gene of interest (protein purification construct gene). The second plasmid provides a T7 lysozyme protein for the tight control of expression. The T7 RNA polymerase gene, under the control of any of the foregoing promoter/operator combinations, can be located on a low copy number plasmid, integrated in the chromosome or supplied by a lambda bacteriophage upon infection. The second plasmid preferably also carries a different genetic marker (i.e., a different phenotypic marker).

In an alternative embodiment, expression in *Bacillus subtilis* can be accomplished by practice of a standard procedure such as those described in Ganesan, A. T., and Hoch, J. A. ed., *Genetics and Biotechnology of Bacilli* Vol. 2, (1987) Academic Press; Winnacker, E. L., *From Genes to Clones* (1987) 209–222, VCH publishers; and Hardy, K. G. and Glover, D. M., ed., *DNA Cloning* (1986) Vol. 2, 1–18, IRL Press Ltd., Oxford, David B. Goeded, *Methods In Enzymology*, 185, American Press, (1990) the disclosures of which are incorporated herein by reference.

The eukaryotic vectors such as those for expression in the yeast, *Saccharomyces cerevisiae*, typically are shuttle vectors which contain an origin of replication for *E. coli* and one for *S. Cerevisiae*, a genetic marker for both cell types, and DNA regulation sequences that will direct the expression in yeast. The regulation sequences typically include a promoter, a regulatory sequence, and a transcription termination signal (including a polyadenylation signal). Optional signal sequences for direction of cellular secretion can also be inserted into the eukaryotic vector.

Typical markers to be incorporated provide positive selection by complementation of mutations in the genes necessary for production of uracil, leucine, histidine, adenine, tryptophan and the like. Promoter sequences which preferably can be incorporated into the eukaryotic vector include alcohol dehydrogenase I or II, glyceraldehyde phosphate dehydrogenase, phosphoglycerokinase, galactose, tryptophan, mating factor alpha and the like.

Expression systems for insect cells include the BEVS system as described in U.S. Pat. No. 4,745,051 the disclosure of which is incorporated herein by reference.

III. A. 3. Transformed Microbe

The microbes used for transfection and transformation with the expression vectors can be prokaryotic or eukaryotic cells based on unicellular or multicellular organisms such as those from mammalian or insect cells. Preferably the unicellular or simple multicellular organisms can be used as a basis for the appropriate host cells. Preferred host cells include *E. coli* and *Saccharomyces cerevisiae* as well as *Spodoptera frupiperda*.

A preferred embodiment, *E. coli* strain BL21(DE3) pLysS, can be used for the two-plasmid prokaryotic system. Other *E. coli* strains are also available and incorporate the characteristics for expression according to the invention. Yeast *Saccharomyces cerevisiae* deficient in the production of several proteases is a preferred embodiment of a eukaryotic host for overproduction of the protein purification construct. Temperature sensitive yeast mutants are available and are included as preferred eukaryotic embodiments.

III. B. Methods for Performing Expression Steps

Recombinant vectors are constructed using standard procedures and protocols for restriction, insertion, ligation, transformation, screening and analysis as described in Sambrook et al., cited supra, the disclosure of which is incorporated herein by reference.

III. B.1 Methods for Forming Recombinant Vectors

The recombinant vector may be formed by restriction of the base vector with a restriction enzyme that is specific for the appropriate restriction site; followed by insertion and ligation of schemes for ultimate construction of the protein purification construct gene. As characterized above, procedures for the restriction, insertion and ligation are found in Sambrook et al., cited supra.

III. B.2 Methods for Multi-unit Gene

Two strategies can be followed for the construction of a multiple unit gene for the variable fused peptide. The first approach involves ligating all the individual gene units and the DNA sequences for the intraconnecting peptides together into an intermediate multi-unit gene. This intermediate multi-unit gene is then transferred to the fusion expression vector by ligating it directly adjacent to the DNA sequence coding for the interconnecting peptide. The second approach involves the sequential ligation of each individual gene unit and the DNA sequence for the intraconnecting peptide into the fusion expression vector. After one such gene unit plus DNA sequence has been inserted, the second one is ligated directly adjacent to the first one, then the ligation is repeated. In both cases, an individual gene unit for one or more a product peptides and the corresponding innerconnecting peptides forming the unit until all units and sequences for intraconnecting peptides are inserted.

III. B.3 Methods for Transforming Host Cells

The transformation procedures fall into several categories depending upon the type of cell to be transformed. Preferred embodiments for transformation of *E. Coli* and *S. cerevisiae* cells include the Mandel, Hanahan and Rothstein protocols. Briefly, the cells are grown to a certain density, at which point they are treated with a solution to render the cell wall or membrane permeable. These cells are then mixed with the recombinant DNA. Upon uptake of the recombinant vectors and recuperation of the cells, transformed cells are screened for the desired characteristics through the use of selection medium.

III. B.4 Method for Control of Expression

The method for expression typically depends on the host transformed with the vector. In one embodiment, induced expression can be practiced by the addition of isopropyl thiogalactoside (IPTG) to the bacterial culture such as *E. coli*. Cells are grown to a desired cell density and then IPTG or lactose is added to induce transcription. Other expression control mechanisms can be practiced through temperature regulation, nutrient starvation or indole acrylic acid influence. For example, the two-plasmid system can be modified to be responsive to temperature, nutrient starvation or indole acrylic acid (IAA) induction of expression. For expression in yeast, identity of carbon source in the growth medium or the incubation temperature can function as a control factor to induce expression. In a preferred embodiment, expression can be induced by recombining the vector with an appropriate temperature sensitive promotor and by either lowering or increasing the incubation temperature. Single- or two-plasmid systems can be regulated in this fashion. Alternatively, temperature control of plasmid copy number may also produce large amounts of the fusion protein through the use of runaway replicons.

The use of an inducible, as opposed to constitutive, expression is important for the purposes of the present invention. hCA is highly toxic to *E. coli* yeast and many other host cells. Establishment of optimum culture density before the protein purification construct expression is triggered minimizes the chance that intracellular accumulation of the expressed protein purification construct will harm the production yield.

III. B.5 Method for Culturation

Following transformation and selection, the cells are cultured to produce optimum quantities of protein purification construct. To grow a mature culture, a volume of suitable medium is inoculated with a single colony of the recombinant clone, grown in suitable growth medium and under appropriate temperature conditions until the cell culture reads the desired density.

III. B.6 Method for Separating

The high affinity of hCAII for sulfanilamide enables a rapid, efficient purification of the protein purification construct. Peptide fusions to the ends of hCAII do not affect the ability of the enzyme to bind to the substrate. The enzymatic reaction site is remote from the chain ends of the enzyme. To perform the binding separation, the culture medium is combined with 0.05M Tris sulfate to adjust the pH to 7.6, and passed through a column of Sepharose covalently bonded to sulfanilamide. The Sepharose-sulfanilamide bonding is accomplished by a Gly-Tyr linker group e.g. Sepharose-Gly-Tyr-sulfanilamide.

III. B.7 Method for Specific Proteins

The purification method for the following protein purification construct example utilizes similar steps for any variable fused polypeptide. The recovery of the desired protein, however, will differ depending upon the interconnecting peptide and cleavage method used. Cleavage will depend on the particular interconnecting peptide and its amino acid sequence as well upon the fact that the product peptide should not contain the amino acid sequence of the interconnecting peptide.

IV. Protocols, Preparations and Examples

The following protocols, preparations and examples further illustrate particular aspects of the invention. They are not meant as limitations of the scope of the invention which is fully set forth above.

IV. A. Synthetic Gene Protocol

1. Peptide and DNA Sequences for the Product Peptides

Table 3, above, provides the peptide and DNA sequences for the preferred embodiments of the product peptide. The oligonucleotides representing these DNA sequences can be synthesized by automated techniques described generally by S. L. Beaucage and M. H. Caruthers, *Tet. Letters*, 221, 859–62 (1981), the disclosure of which is incorporated herein by reference. Typically, a Vega Coder 300 DNA synthesizer or a ABI model 380B can be used. Alternatively, native DNA coding for the desired protein can be isolated by known purification techniques described in Sambrook et al., cited supra the disclosure of which is incorporated herein by reference.

IV. B. Protocols for Insertion, Transformation

Procedures for methods to restrict, ligate, transform, select, culture, and lyse according to the invention, generally follow standard methods known in the art. Literature providing the details for these methods include, Sambrook et al., cited supra. The textual material of each of these references is incorporated herein by reference.

In a preferred embodiment DNA sequences can be ligated together according to the procedure described in Sambrook et al., cited supra.

IV. B. 1. Restriction Protocol a. Digesting DNA with Restriction Endonucleases

Typically, 0.5 to 2 ug of plasmid DNA is digested in 20 ul of a 1X restriction buffer with 1–20 units of restriction enzyme. The reaction mix is incubated for 1 to 16 hours at the temperature recommended by the enzyme supplier. The reaction mix is then either size fractionated by gel electrophoresis or the DNA is further purified by standard procedures as described in Sambrook et al., cited supra.

IV. B. 2. Insertion and Ligation Protocol

Typically, the cloning vector is digested with the appropriate restriction enzymes as described in the foregoing restriction protocol. The linearized vector can then be dephosphorylated with calf intestinal phosphatase (CIP) or bacterial alkaline phosphatase (BAP) under conditions known to those of skill in the art, e.g., as suggested by the supplier. The DNA is then further purified by standard procedures (see Sambrook et al., cited supra), which usually involve a phenol extraction and ethanol precipitation.

The DNA segment to be inserted is then mixed in a 3–5 fold (for large fragments) or 20–30 fold (for short oligonucleotides) molar excess with this precut cloning vector. The ligation is performed in a 1× ligation buffer (20 mM Tris pH 7.6, 10 mM $MgCl_2$, 0.4 mM beta-mercaptoethanol, 0.4–1.0 mM ATP), in the presence of T4 DNA ligase, at 16° C. for 16 hours. An aliquot of the reformed vector is then used to transform competent *E. coli* cells and select for recombinant plasmids.

IV. B. 3. Transformation Protocol for *E. Coli*

In a preferred embodiment, the recombinant vector can be taken up by *E. coli* according to the calcium chloride procedure given below. The alternative transformation protocol can also be used.

a. Bacterial Transformation by the Calcium Chloride Procedure (Mandel Protocol)

This procedure will transform (prokaryotic) bacteria with plasmid DNA (after Mandel and Higa 1970).

After inoculating Luria broth (described by Sambrook et al., cited supra) with a bacterial culture, the cells are grown with agitation at optimum temperature to a density of about $5 \times 10^5$ to $10^7$ cells/ml. The culture is chilled to about 0° C., centrifuged and the cells collected. The cells are then resuspended in an ice-cold, sterile solution of 50 mM $CaCl_2$ and 10 mM Tris-Cl (pH 8.0). This centrifuge and resuspension step is repeated one more time. The result is a concentrated suspension of treated cells that are ready to accept the new vector.

For maximum transformation efficiency, the bacterial culture preferably is in a logarithmic phase of growth; the cell density preferably is low at the time of treatment with calcium chloride; and the treated cells preferably are maintained at 4° C. for 12–24 hours. To take up the vector, an aliquot of the ligation reaction is added to the suspension of treated cells. The combination is mixed and stored on ice for a short time. Up to 40 ng of DNA (dissolved in up to 100 µl of ligation buffer or TE) can be used for each transformation reaction.

Next, the transformed cells in culture tubes are transferred to a 42° C. water bath for 2 min. An aliquot of L broth is added to each tube and the cells incubated at 37° C. for about 30 minutes (tetracycline selection) or 1 hour (ampicillin or kanamycin selection). This period allows the bacteria to recover and to begin to express antibiotic resistance. The cells are spread onto selective media and are incubated at optimum temperature. Colonies will appear overnight. (Adapted from Sambrook et al., cited supra.)

b. Alternate Transformation Protocol

Several colonies can be removed from a freshly streaked SOB agar plate (i.e., Luria broth supplemented with magnesium chloride, -sulfate and potassium chloride) and dispersed in SOB medium. The cells are inoculated into an Erlenmeyer flask containing SOB medium and incubated at optimum temperature with moderate agitation until the cell density is about $4-7 \times 10^7$ viable cells/ml. The culture is then collected and chilled on ice for a short time. The cells are pelleted by centrifugation at 750–1000 g at ice temperature. The cells are resuspended in culture volume of transformation buffer (TFB) and incubated on ice for a short time. The cells are repelleted and drained thoroughly as before, then resuspended in TFB.

To adapt these cells to accept transformation, a DMSO and dithiothreitol DTT solution (DMSO and DTT (DnD)) is added to the cells. The cells are then incubated on ice for a short time. A second, equal aliquot of DMSO and DTT (DnD) as above is added to give about a 7% final concentration. The cells are incubated on ice for 10–20 minutes.

To obtain transformation, chilled cells and the vector DNA solution are combined in a volume of less than 20 µl. The cells are incubated on ice for a short time, then heat shocked by placing them in a water bath at about 42° C. for 90 seconds. These cells are returned onto ice to quench the heat shock, allowing 2 minutes for cooling. SOC SOB with glucose medium is added to each culture and the cultures incubated at about 37° C. with moderate agitation for 30–60 minutes. The cells are then spread on agar plates containing appropriate additives to select transformants.

IV. B. 4. Transformation Procedure for Yeast

Recombinant plasmids are constructed using *E. coli/S. cerevisiae* shuttle vectors. These plasmids are capable of replicating in both hosts. An aliquot of the ligation mixture is used to first transform an *E. coli* host. Recombinant clones are analyzed (using standard procedures described in Sambrook et al., cited supra) and positive ones identified. Plasmid DNA is isolated from these clones (according to procedures described in Sambrook et al., cited supra) and used to transform the yeast host. Several transformation procedures exist for yeast. The two mainly used are the spheroplast- and lithium method, and are described below. Both are adapted from Rothstein, R., *DNA Cloning* (Glover DM. Ed) vol. 2, pp. 45–66, IRL Press Ltd., Oxford (1986).

Yeast cells are grown to a density of $1-2 \times 10^7$/ml in yeast extract, peptone, dextrose (YPD) liquid medium. The cells are washed twice with sorbitol solution by repeated pelleting followed by cell resuspension and a final resuspension in sorbitol and A-mercaptoethanol.

A diluted aliquot is plated on YPD solid medium. This will serve as the control to calculate the percentage of killing after spheroplast formation. Glusulase enzyme (Endo Laboratories, Inc.) is added to the final suspension and incubation is conducted at 30° C. with gentle shaking for about 40 minutes. An aliquot is taken again on YPD medium to measure the percentage survival after spheroplast formation.

The cells are prepared for transformation as follows. The spheroplasts are pelleted and then gently resuspended in sorbitol solution. This procedure is repeated several times followed by resuspension of the spheroplasts in sorbitol solution. Tris-HCl pH 7.4 and 0.1M $CaCl_2$ solution are then added. The spheroplasts are pelleted and resuspended in sorbitol solution, 10 mM $CaCl_2$.

To transfer the spheroplasts, aliquots are distributed and vector DNA (1–10 Ĩg) added while keeping the total volume of DNA added to less than 20 Ĩl. The cells and DNA are incubated for a short time at room temperature, then resuspended and combined with 2 ml of 50% (w/v) polyethylene glycol mixed with 0.2 ml of 0.1M Tris-HCl, pH 7.4 and 0.1M $CaCl_2$. After 10 minutes at room temperature, the spheroplasts are pelleted, resuspended in sorbitol solution, 10 mM Tris-HCl, pH 7.4 and 10 mM $CaCl_2$. The spheroplasts are plated in regeneration agar (maintained at 45°–50° C.) onto the appropriate omission medium.

IV. B. 5. Alternative Lithium Transformation Procedure for Yeast

A culture of yeast is grown in YPD medium. The cells are pelleted and then resuspended in tris EDTA (TE). The resuspended cells are treated with 0.1M LiCl (or 0.3M LiOAc) in TE and incubated at 4° C.

To transform the cells, 200 Ĩl of cells per transformation reaction are combined with 1–10 Ĩl of vector DNA, keeping the volume of DNA added to less than 1/10 the total volume. The cell-DNA mixture is incubated for 30 minutes at room temperature. The cells are resuspended in medium and then 1.5 ml of 40% polyethylene glycol is added. The mixture is incubated at room temperature. The cells are heat shocked at 42° C. for 5 minutes, and then centrifuged. The cell pellets are washed with water by repeatedly centrifuging and gently resuspending. Finally, the cells are resuspended in water and plated on appropriate omission medium. Adapted from Rothstein, cited supra.

IV. C. Selection Protocol

In a preferred embodiment, transformed clones can be selected by their phenotype (antibiotic resistance) by plating on selective medium containing appropriate amounts of antibiotics.

Transformed *E. coli* are selected through the use of plates containing the appropriate antibiotic (i.e., the one to which resistance is conferred by the introduced plasmid). Typical final concentrations are: ampicillin at 100 ug/ml, chloramphenicol at 10 ug/ml, kanamycin at 50 ug/ml, streptomycin at 25 ug/ml tetracycline at 15 ug/ml. When using *E. coli* BL21(DE3)pLysS as the host, transformants are plated out on medium containing both ampicillin and chloramphenicol (at the above concentrations).

Transformed *S. cerevisiae* cells are selected through the use of nutrient omission plates (described by Rothstein, cited supra) lacking uracil, tryptophan, leucine, histidine or adeninse (depending on the plasmid and host that is used).

IV. D. Culturing Protocol

In a preferred embodiment, the method for culturing cells can be practiced as described in Sambrook et al., cited supra. Briefly, the method entails transferring a single bacterial. colony to a small volume (3–5 ml) of bacterial growth medium (such as Luria Broth) containing an appropriate antibiotic. The culture is incubated at 37° C. (or other appropriate temperature) and scaled up to larger volumes. Yeast cells are cultured similarly, using yeast omission medium and incubating the cells at 30° C.

IV. E. Lysing Protocol

In one embodiment, cells can be lysed with lysozyme according to the protocol as follows:

1. Lyse the cells in 1/10 th the volume of the original culture of 50mMTris (pH 7.9)-½ mM EDTA containing 1 mg/ml lysozyme. Keep on ice for 60 minutes.

2. To the now viscous suspension, add: $MgCl_2$ to a final concentration of 10 mM, RNAase to 1–2 ug/ml, and DNAase to 5 ug/ml. Incubate on ice for 30–45 minutes. (until the solution is no longer viscous).

3. Spin at 4 C/10000 rpm (SS34 rotor)/5 minutes. Save the supernatant.

In another embodiment the cells can be lysed by a single freeze-thaw cycle provided that the BL21(DE3) pLysS host is used or any other host containing the pLysS plasmid.

IV. F. Ligand Immobilized Affinity Separation Protocols and Preparations

An aspect of the purification sequence for the protein purification construct involves immobilization of sulfanilamide when hCAII is the affinity binding agent. In this case, three kinds of sulfonamide affinity substrates, three linking methods, two matrices and two ways of eluting the hCA are exemplified. These protocols are given below, however, there are many possibilities for combinations of immobilization matrix, substrate and linker.

The first method uses a polyamide matrix, 1-ethyl-3(3 dimethylaminopropyl)carbodiimide acid as the linking agent and p-amino methyl benzene sulfonamide as the affinity substrate. Elution of the bound protein is accomplished with $NaN_3$.

IV. F. 1. Protocol A

Formation of Immobilized Sulfanilamide a. Materials
  a. A polyamide gel such as CM BioGel A (from BioRad, Inc.)
  b. 1-ethyl-3(3 dimethylaminopropyl)carbodiimide
  c. p-AminoMethyl Benzene Sulfonamide (pAMBS)
  d. Acetone, Carbonate, Bicarbonate, Tris. $K_2SO_4$ b. Coupling Reaction The reaction to couple sulfanilamide to the solid support may be conducted in the following manner. The gel is washed several time with $H_2O$, then with 50% Acetone-water. The washed gel is placed in a 1-liter flask and 50% acetone-water is added to form a slurry. pAMBS (3 g) is dissolved in 50% Acetone-$H_2O$ at pH 4.8 and the solution is added to the slurry to form a component mixture.

To mobilize the pAMBS, EDAC (5 g) is dissolved in $H_2O$ to form an EDAC solution just prior to the coupling reaction. The EDAC solution is added dropwise to the component mixture at room temperature while maintaining the pH at 4.8 by HCl addition. After all EDAC is added the pH is kept at pH 4.8 for about 6–8 hours, the reaction is stirred at ambient temperature and allowed to proceed for a total of 20 hours.

c. Washing

The coupled gel is washed in a fretted disk funnel with the following sequence of solutions.
a. 150 ml 50% Acetone-water;
b. 1 liter water;
c. 1.5 liter hot Carbonate-Bicarbonate (1:1);
d. 150 ml 50% Acetone-water;
e. 700 ml Acetone;
f. 2 liters water; and
g. 1 liter of 0.1M Tris, 0.2M $K_2SO_4$ at pH 9.0.

d. Gel Storage

The gel is kept in Tris buffer at pH about 7.5 with a trace of azide to prevent bacterial growth.

The second method employs a Sepharose matrix, to which p-aminobenzenesulfanilamide is coupled via a glycyl-L-tyrosine spacer arm. The bound hCA (or protein purification construct) is eluted with potassium thiocyanate.

IV. F. 2. Protocol B

Sepharose-Gly-Tyr may be prepared from Sepharose 4 B freshly activated with cyanogen bromide (180 mg/ml packed Sepharose) by coupling with Gly-Tyr (5 mg/ml packed Sepharose) in 0.1M-sodium bicarbonate, pH 9.5. The affinity gel is obtained by diazotization of p-aminobenzenesulfanilamide and coupling of this compound to the Sepharose-Gly-Tyr. p-aminobenzenesulfanilamide (0.3 g) is suspended in 120 ml of ice-cold 1M-HCl, and to the suspension is added 0.9 g of sodium nitrite in 45 ml ice-cold water. After 10 minutes of reaction the diazotized benzenesulfanilamide is poured into a 600 ml suspension, containing 300 ml packed Sepharose-Gly-Tyr in 0.2M-sodium bicarbonate pH 8.8. The pH is adjusted to 9.5 with 1M-NaOH and, after gentle stirring for 3 hours at room temperature, the coupled red Sepharose derivative (SA-Sepharose) can be washed with 10 liters of water and 2 liters of 0.05M-Tris-sulfate pH 7.6.

IV. F. 3. Protocol C

The third method uses the same Sepharose matrix described above, except that the ligand is p-carboxybenzenesulfanilamide and it is coupled to the resin with ethylenediamine.

The Sepharose-ethylamine derivative may be prepared by adding 115 ml of an aqueous solution containing 15 ml ethylene diamine, adjusted to pH 10 to 100 ml freshly activated packed Sepharose. The affinity gel is prepared by coupling p-carboxybenzenesulfanilamide to the Sepharose ethylamine by the carbodiimide method. One hundred milliliters of wet packed Sepharose was suspended in 400 ml dimethylformamide containing 1 g of p-carboxybenzenesulfanilamide. A portion of EDC (5 g in 30 ml water pH 4.7) is added slowly, and the pH maintained at pH 4.7. After 20 hours of reaction at room temperature the affinity gel, Sepharose-ethyl(p-carboxybenzenesulfanilamide) carboxamide (SE-Sepharose) can be washed with dimethylformamide and a large volume of water.

IV. F. 4. Separation Procedure

To separate under Protocols A, B and C, the following procedure can be used. The lysate from the cell culture is first pumped through a column with the SA-Sepharose equilibrated with 0.05M-Tris-sulfate pH 7.5. After washing with 0.05M-Tris-sulfate-1M-sodium sulfate pH 7.5 to remove other material, the protein purification construct (containing carbonic anhydrase), can be eluted with 0.2M-potassium thiocyanate in 0.05M-Tris-sulfate pH 6.5.

IV. G. Protocols for Cleaving

The methods for cleaving the inter, intra and innerconnecting peptide depend upon the amino acid sequence of the inter, intra and innerconnecting peptide.

1. Protocol A

Enterokinase cleavage ($Asp_4Lys$ sequence)

The fusion protein eluted from the column is made 10 mM in Tris (pH 8.0). Bovine enterokinase is prepared as a 100 ug/ml 10mM Tris (pH 8.0) stock solution. An appropriate aliquot is added to the fusion protein solution (10% by weight) and incubated at 37° C. for 15 hours.

2. Protocol B

Factor Xa (IleGluGlyArg)

Cleavage can be performed on ice by combining enzyme and substrate at a ratio of 1:200 (wt/wt) and allowing the reaction to proceed for 12 hours in 50 mM Tris (pH 8.0)/100 mM NaCl.

3. Protocol C

Thrombin (ArgGlyProArg or resembling Structures like ArgAlaProLys)

Thrombin cleavage can be performed while the fusion protein is still attached to the affinity resin. Thrombin is then added at a concentration of 1% (w/w fusion protein) and incubated for 1 hour at 37° C.

4. Protocol D

Collagenase

Purified collagenase of *Achromobacter iophagus* is dissolved in 10 mM Tris/0.25M NaCl/10 mM $CaCl_2$/10 mM 2-mercaptoethanol, final pH 7.4 at a concentration of 1 mg/ml. Ten mg of protein purification construct protein at a concentration of 0.5–3 mg/ml is digested with 10 ul of the collagenase stock solution for 10 min. at 30½C. Consensus collagenase cleavage site:

-Pro-Xxx-Gly-Pro-Yyy

4. Protocol E

Ubiquitin cleaving protein (ArgGlyGly)

Cleavage reactions can be performed by combination of the enzyme and substrate at an appropriate ratio allowing the reaction to proceed for 12 hours.

5. Protocol F

CNBr (Methionine) Chemical Cleavage

The protein is dissolved at a concentration of 10–20 mg/ml in 70% formic acid, CNBr is added to a final concentration of 2 mg reagent per mg polypeptide, and the mixture is incubated for 18–20 hours at ambient temperatures. This method is limited to desired proteins that are stable in 70% formic acid and do not contain methionine residues within their amino acid sequences.

6. Protocol G

Hydroxylamine (AsnGly)

A solution of 2M hydroxylamine hydrochloride and 0.2M trisbase is titrated to pH 9.0 at 45° C. The fusion protein is dissolved in this solution at 45° C. for 4 hours. The reaction is terminated by lowering the temperature degree and adjusting the pH to below 8.0.

7. Protocol H

Chemical Cleavage at Cysteine Residues

The fusion protein is dissolved in 100 mM Tris (pH 8.0)/5mM DTT. 2-Nitro-5-thiocyanobenzoate is then added and the reaction is allowed to proceed for 20 minutes at room temperature. Raising the pH to 9.0 ensures cleavage at the N-terminal side of the now modified cysteine residue.

8. Protocol I

Cleavage with *Staphylococcus Aureaus* V8 Protease

10 ìg of fusion protein is digested with 1 ìg of protease at 37° C. in 50 mM ammoniumbicarbonate (pH 7.8) for up to 18 hours.

9. Protocol J

Renin Cleavage

The fusion protein is dissolved in 50 mM sodiumphosphate (pH 7.1), 5 mM EDTA, 5 mM sodiumtetrathionate. Renin is added at a ratio of 1:1000 to the fusion protein and the mixture is incubated at 37° C. for 16 hours.

10. Protocol K

Cleavage at Tryptophan Residues with BNPS-skatole

The fusion protein is dissolved in 50% acetic acid at a concentration of 10 mg/ml. A freshly prepared solution of BNPS-skatole (2-(2-nitrophenylsulfenyl)-3-methyl-3-bromoindolenine) in acetic acid is added at a 100-fold molar excess (versus tryptophan residues in the protein). The mixture is incubated at room temperature for 48 hours in the dark. Tyrosine can be added as a scavenger.

IV. H. Final Separation Protocol

After the desired protein is cleaved from the hCAII moiety by a chemical or enzymatic method, separation of the constituents can be made by means known to those of skill in the art. For example, the chemical method produces upon cleavage two proteins, the hCAII with attached interconnecting peptide and the variable fused polypeptide. The hCAII plus interconnecting peptide can be removed by chromatography on a sulfanilamide column. The variable fused polypeptide elutes from the column.

For the enzymatic method, the cleavage mixture contains three proteins, hCAII plus the attached interconnecting peptide, the variable fused polypeptide, and the protease (cleaving enzyme). hCAII can be removed by sulfanilamide immobilization as above. The protease can be separated from the variable fused polypeptide by use of the chemical and/or physical properties of the desired peptide and protease including size exclusion, ion exchange or affinity chromatography.

V. Examples

EXAMPLE 1

Synthesis of Gene and Vectors

Five different plasmids were constructed, all of which coded for a human carbonic anhydrase II (CAII) C-terminal fusion protein. Each plasmid included the gene for the foregoing fusion protein under the transcriptional control of the T7 promoter. The fusion protein itself consisted of a truncated hCAII protein which lacked the C-terminal three amino acids, followed by the enterokinase recognition sequence (ValAspAspAspAspLys), followed by the protein of interest. The five genes that were fused onto the CAII gene code for angiotensin (a ten amino acid (AA) protein), a calcitonin derivative (a 32 AA protein), bovine caltrin (a 47 AA protein), the delta subunit of the *E. coli* ATPase (a 174 AA protein) and the epsilon subunit of the *E. coli* ATPase (a 173 AA protein). The first three genes were encoded by synthetic genes, the last two were isolated from the previously cloned unc operon. The synthetic genes were designed using optimal codon usage for *E. coli* and contain unique and useful restriction sites for future alterations. The expression system that may be used initially uses the T7 promoter to direct transcription of the fusion gene by a chromosomally encoded T7 RNA Polymerase which is produced upon induction by isopropylthiogalactoside (IPTG).

In an alternate system, the gene for T7 RNA Polymerase could be encoded by a second plasmid. This gene could under the transcriptional control of any promoter compatible with the host cell (e.g. a temperature inducible promoter, a tryptophan promoter etc.).

Construction of p0304:

All clones were derived from the parent vector pET31F1mHCA2. The T7 expression cassette of pET-3c (described by Rosenberg, A. H., Lade, B. N., Chui, D., Lin, S. W., Dunn, J. J., and Studier, F. W. *Gene* 56, 125–135 (1987) was cloned into a truncated pSP64. This truncated pSP64 already contained a DNA segment encoding the F1 origin. The gene coding for human carbonic anhydrase II (hCAII) was then transferred to this expression cassette and yielded pET31F1mHCA2. This vector was used as the basis for the construction of the fusion vector p0304. For this purpose, two complementary oligonucleotides with the following sequence were synthesized: 5'-AGCTTTCGTTGACGACGACGATATCTT-3' and 5'-AGCTAAGATATCGTCGTCGTCAACG-3'. Upon phosphorylation of each oligonucleotide (following the procedures of Sambrook et al., cited supra), they were pooled, heated to 80° C. and cooled slowly to room temperature to allow for annealing. This double-stranded oligonucleotide coded for the first five amino acids of the enterokinase recognition sequence. It also contained a unique EcoRV site and HindIII cohesive termini. The sequence of the oligonucleotide was such that, upon insertion of this oligonucleotide into a HindIII site, only the 5'-end HindIII site was recovered. This double-stranded oligonucleotide was then ligated into the parent vector which had been digested with HindIII and dephosphorylated with calf intestinal phosphatase (CIP) following the procedure of Sambrook et al., cited supra. The ligation was performed at 16° C. for 16 hours. *E. coli* K-12 strain SB221 was made competent by the $CaCl_2$ (as described in Sambrook et al., cited supra) and transformed with an aliquot of this ligation mixture. Plasmid DNA was isolated from single colonies by the alkaline lysis method (described in Sambrook et al., cited supra), and analyzed with restriction enzymes. The orientation of the oligonucleotide could be verified using the HindIII site. One such positive clone was denoted p0304 which now served as the parent vector for the construction of fusion genes. p0304 coded for hCAII fusion protein in which the C-terminal three amino acids of hCAII were replaced by part of the enterokinase recognition sequence. The oligonucleotide introduced a unique EcoRV site, which may be used as the cloning site for the construction of fusion genes. If the gene cloned into this EcoRV site starts with a Lysine codon, then the enterokinase recognition sequence is created.

Construction of Several Additional Fusion Genes:

p0304Ang. Two complementary oligonucleotides (5'-AAAGACCGTGTATACATCCATCCGTTC-CATCTGTAAGAT-3' and 5'-ATCTTACAGATGGAACG-GATGGATGTATACACGGTATTT-3') were synthesized. Phosphorylation and annealing as described above, resulted in a double-stranded oligonucleotide with blunt ends and an internal AccI site. This piece of DNA was then cloned into the unique EcoRV site of p0304. Clones were analyzed as above, and one positive clone was named p0304Ang. This plasmid contained a fusion gene that coded for a truncated hCAII protein (minus the last three amino acids), fused C-terminally to an enterokinase recognition sequence followed by the angiotensin peptide.

p0304Cal. pINMetCal8 is bacterial expression plasmid that contains a synthetic gene that codes for bovine caltrin (Van Heeke, G.; *Ph.D., Dissertation,* 1989 University of Nebraska, Lincoln). The gene starts with a methionine codon and has an EcoRV site immediately upstream of it. Digestion of this plasmid with EcoRV and BamHI released a fragment containing the entire caltrin coding sequence including the methionine codon and a 3' untranslated region of about 150 bp. This reaction mixture was treated with T4 DNA polymerase to flush the BamHI overhang and the caltrin containing fragment was cloned into the EcoRV site of p0304. This resulted in an in-frame alignment of the caltrin gene with the hCAII gene. Restriction enzyme analysis was used to determine the presence and orientation of the insert. One positive clone was named p0304Cal. It contained a fusion gene that coded for hCAII (minus the last three amino acids), linked to Met-caltrin via a Val-$(Asp)_4$ peptide. The enterokinase recognition sequence was not recovered, however, CNBr treatment can be used to cleave the caltrin portion of the fusion protein.

p0304delta. A DNA fragment containing the gene coding for the delta subunit of the *E. coli* $F_1$ $F_0$-ATPase was isolated from pRPG51 (described by Gunsalus, R. P., Brusilow, W. S. A., and Simoni, R. D. *Proc. Natl. Acad. Sci. USA* 79, 320–324 (1982)). The delta gene was isolated from pRPG51 and subcloned into pTZ18R. A unique EcoRI site was introduced near the 5' end of the gene using site-specific mutagenesis (as described in Sambrook et al., cited supra). A synthetic oligonucleotide that restored the 5' end sequence and added a lysine codon as part of a DraI site, was cloned into this EcoRI site. This resulted in plasmid pSMS2.3-5, which was then digested with DraI and HindIII, treated with T4 DNA polymerase, and the desired fragment was cloned into the EcoRV site of p0304. As above, restriction analysis was used to confirm the presence and orientation of the insert. A positive clone was denoted p0304delta. It coded for the aforementioned truncated hCAII protein attached to the delta subunit via an enterokinase linker peptide (Val-$(Asp)_4$Lys).

p0304eps. A similar route was followed for the epsilon subunit of the *E. coli* $F_1F_0$-ATPase. The gene coding for the epsilon subunit with a lysine attached to its N-terminal end was isolated from pRPG53Eol. This plasmid itself was derived from pRPG53 (Gunsalus et al., cited supra). It had a lysine codon as part of a DraI restriction site immediately upstream of the start codon. Digestion with DraI released this fragment, which was then inserted into the EcoRV site of p0304. The new plasmid, named p0304eps, coded for the epsilon subunit linked to hCAII via an enterokinase recognition sequence.

p0304Calcit. A synthetic gene that coded for a calcitonin derivative was constructed using six separate oligonucleotides. The gene was designed using optimal codon usage for *E. coli* and had restriction sites edited at regular spacing. The complete sequence is provided below. The synthetic gene was first assembled in pTZ18R. The coding sequence was designed such that a DraI site was present immediately upstream of the start signal and an EcoRV site downstream of the stop codon. An extra Ala codon was added at the 3' end, followed by a stop codon. The DraI site also introduced a lysine codon directly adjacent to the cysteine. The gene was then transferred as a DraI/EcoRV fragment to the EcoRV site of p0304. This created an in-frame alignment of the calcitonin gene with the hCAII gene. Upon expression, a fusion protein was produced that had the calcitonin-like peptide linked to hCAII via the enterokinase recognition sequence.

Sequence for the synthetic Calcitonin derivative:
5'-AAGCTTTAAATGCGGTAACCTGTCGACT-TGCATGCTGGGTACCTAC ACTCAAGATCTGAA-

CAAATTTCATACTTTCCCGCAGACATC-
GATAGGTGTTGGAGCTCC
GGCTTAAGATATCGGATCC-3'.

All examples below describe experiments involving the angiotensin protein purification construct.

EXAMPLE 2

Transformation of *E. coli* with the Recombinant vector

*E. coli* was transformed according to standard procedures as described in Sambrook et al., cited supra (also see protocols above). *E. coli* K-12 SB221 was transformed with an aliquot of the ligation mix by the calcium chloride method described above.

EXAMPLE 3

Selection of recombinant cells

Transformed cells were plated on Luria broth medium containing 100 ug/ml ampicillin and incubated at 37° C. for 16–18 hours.

EXAMPLE 4

Selection of Desired Recombinant Vector

Single colonies were grown in 3–5 ml liquid Luria broth containing 50 ug/ml ampicillin, and plasmid DNA was isolated using the minprep alkaline lysis method (Sambrook et al., cited supra). Plasmid DNA was analyzed with restriction enzyme AccI which indicated the presence of the oligonucleotide coding for angiotensin. A second restriction enzyme analysis with PstI and EcoRV revealed the orientation of the inserted oligonucleotide. The junction region of a plasmid construct with the oligonucleotide in the correct orientation was then further verified by DNA sequencing and a positive clone was named p304Ang. This plasmid was then used to transform *E. coli* BL21(DE3)pLysS (as in Example 3). Transformed cells were recovered on Luria broth plates containing both ampicillin (100 ug/ml) and chloramphenicol (10 ug/ml). These cells were then used for the overproduction of protein purification constructs.

EXAMPLE 5

Culturing and production of protein purification construct

Transformed cells (BL21(DE3)pLysS containing p0304Ang were grown in 3–5 ml Luria broth containing ampicillin and chloramphenicol at 37° C. for 16–18 hours. The culture was then diluted 1 to 100 in fresh medium and grown until the optical density reached 0.8–1.0. At this point, IPTG (see above) was added to a final concentration of 0.05–0.4 mM or lactose was added to a final concentration of 0.2 to 2 percent. The culture was further incubated at 21°–37° C. for 2–16 hours.

EXAMPLE 6

Lysing mature culture of host cells

The cells were harvested by centrifugation and washed in ice-cold 50 mM Tris pH 8.0. The cell pellet was then frozen at −20° C. Upon thawing of this pellet and resuspension in 50 mM Tris pH 8.0, the cells lysed on their own. The viscous cell extract was then treated with DNase (0.5 ug/ml) and RNase (1 ug/ml) in the presence of 10 mM $MgCl_2$ at 0° C. for 45–60 minutes. The cell extract was spun to remove cellular debris and the recovered supernatant fraction was subjected to affinity chromatography. Alternatively, the viscosity can be reduced by repeated passage of the cell extract through a syringe needle.

EXAMPLE 7

Alternate cell lysis, affinity chromatography and enzyme cleavage.

The protein purification construct product can be isolated by column or batch-wise affinity chromatography. *E. coli* cells containing the protein purification construct incorporating angiotensin were freeze-fractured or freeze-thawed to release catalytic amounts of lysozyme expressed by the plasmid vector. The lysozyme lysed the remainder of the cells. This process was carried out in 0.05M-Tris-sulfate 7.5. It was centrifuged to 20,000×g to remove any remaining particulate matter.

The dialyzed material was then added to a 10 mL column of affinity resin prepared with sulfanilamide as described above and previously equilibrated to 0.05M-Tris-sulfate pH 7.5. The column was eluted with the same buffer. The majority of the protein in the cell extract did not adhere to the column and came through in the void volume. The column was washed and until all 280 nm absorbing material had eluted from the column. It was then washed with 0.05M-Tris-sulfate, 1M-sodium sulfate pH 7.5 to remove any protein material which had adhered to the column by adventitious bonding. The column was then eluted with 0.2M-potassium thiosulfate 0.05M-Tris-sulfate pH 6.5 to remove the protein purification construct, i.e., angiotensin. The protein purification construct was collected and dialyzed to remove the 0.2M potassium thiosulfate against the desired buffer. This material was then subjected to an analysis by electrophoresis procedures which confirmed its identity and subsequently reacted with enterokinase to cleave the $Asp_4Lys$ bond to liberate the desired, cloned angiotensin.

EXAMPLE 8

Partition chromatography of protein purification construct peptide and cleavage enzyme Size exclusion chromatography was used to separate the cleavage enzyme from the desired peptide. Alternatively, an affinity substrate for either the peptide or the cleavage enzyme can be used.

EXAMPLE 9

Construction of a Multi-unit Gene for Cholecystokinin-8

This is an example of the construction of a multi-unit gene for the peptide cholecystokinin-8.

Two sets of oligonucleotides are synthesized. An oligonucleotide with the following sequence, 5'-AAAGAT-TATATGGGTTGGATGGATTTTAAATAAGAT-3', and an oligonucleotide with the complementary sequence constitute the first set. This DNA fragment codes for the cholecystokinin-8 peptide with an added C-terminal lysine. Downstream of the lysine codon (AAA) is a stop codon (TAA) followed by the first half of an EcoRV restriction enzyme site (GAT). The additional C-terminal lysine constitutes the intraconnecting peptide. Upon phosphorylation and annealing of these oligos (see above examples), this double-stranded DNA fragment is ligated into the single EcoRV site of the fusion expression vector p0304. Insertion of this fragment can be monitored by the presence of the internal DraI (TTTAAA) restriction enzyme site. Correctness of orientation can be verified by restriction enzyme analysis, since an EcoRV site will be reconstructed at the 3' end of the gene. At this point, the variable fused peptide consists of a single copy with an extra lysine at the C-terminal end. A third oligo with the sequence 5'-AAGGATTATATGGGT-TGGATGGATTTT-3' and its complementary oligo are then phosphorylated, annealed and cloned into the DraI restriction enzyme site of the previously cloned DNA fragment. Only one DraI site will be restored upon insertion, since the codon for lysine, now at the 5' end, was changed to AAG (instead of AAA). The restored DraI site is therefore useful for determining the orientation of the inserted oligo. At this point, the variable fused peptide consists of two copies. These steps can be repeated until the desired copy number is obtained. The multicopy gene construct then codes for a large polypeptide which consists of a string of cholecystokinin-8 peptides each linked together by a lysine residue. The large polypeptide can be released from the protein purification construct by enzymatic cleavage at the enterokinase recognition sequence. The individual cholecystokinin-8-lysine fusion product peptides can then be obtained upon trypsin cleavage. The cholecystokinin-8 peptide is then recovered from the lysine fusion product peptide through the action of carboxypeptidase. Free lysine can be removed by ion exchange chromatography on Dowex-50.

We claim:

1. A method for expressing a protein purification construct of three, tandem, coupled segments, the first segment being a binding protein, the second segment being an interconnecting linker, and the third segment being a variable fused polypeptide, comprising:

inserting an expression vector carrying a recombinant gene for the protein purification construct into a compatible host cell to produce a transformed host cell; and causing the transformed host cells to express the protein purification construct;

wherein;

the recombinant gene comprises base segments coding for the segments of the protein purification construct;

the base segment for the binding protein codes for mammalian or human carbonic anhydrase or a modified version of the mammalian or human carbonic anhydrase;

the modified version of the carbonic anhydrase a) has an amino acid sequence that is free at least of the amino acid segment for the interconnecting linker, b) has a dissociation constant for a mammalian or human carbonic anhydrase inhibitor that is no greater than about $10^{-7}$M, and c) the amino acid sequence of the modified version of carbonic anhydrase is the amino acid sequence of human or mammalian carbonic anhydrase that has been modified by a change selected from the group consisting of: elimination of methionine residues, replacement of one or more glutamate residues with another amino acid residue, replacement of one or more arginine residues with another amino acid residue, replacement of one or more asparagine residues with another amino acid residue, replacement of one or more methionine residues with another amino acid residue, replacement of one or more cysteine residues with another amino acid residue, and any combination thereof; and, the base segment for the variable fused polypeptide codes for a single polypeptide unit or multiple copies of the polypeptide units with adjacent polypeptide units being linked by an intraconnecting linker, the polypeptide unit being one copy of a product peptide or multiple copies of the product peptide with adjacent product peptide copies being linked by an innerconnecting linker.

2. A method for purifying a polypeptide product from a recombinantly expressed protein purification construct of three, tandem, coupled segments, the first segment being a binding protein, the second segment being an interconnecting linker, and the third segment being a variable fused polypeptide, comprising:

contacting an immobilized ligand for the binding protein with a mixture containing the protein purification construct and cellular constituents from a culture of transformed cells which has expressed the protein purification construct to produce a bound protein purification construct conjugated to the immobilized ligand;

removing the unbound cellular constituents from the bound protein purification construct to produce a segregated protein purification construct;

treating the segregated protein purification construct with a cleavage reagent for the interconnecting linker to produce a free, variable fused polypeptide as the polypeptide product and recovering the free, variable fused polypeptide as the polypeptide product, wherein;

the binding protein is mammalian or human carbonic anhydrase, or a modified version of mammalian or human carbonic anhydrase;

the modified version of the carbonic anhydrase a) has an amino acid sequence that is free at least of the segment for the interconnecting linker, b) has a dissociation constant for a mammalian or human carbonic anhydrase inhibitor that is no more than about $10^{-7}$M., and c) the amino acid sequence of the modified version of carbonic anhydrase is the amino acid sequence of human or mammalian carbonic anhydrase that has been modified by a change selected from the group consisting of: elimination of methionine residues, replacement of one or more glutamate residues with another amino acid residue, replacement of one or more arginine residues with another amino acid residue, replacement of one or more asparagine residues with another amino acid residue, replacement of one or more methionine residues with another amino acid residue, replacement of one or more cysteine residues with another amino acid residue, and any combination thereof; and, the variable fused polypeptide is a single polypeptide unit or multiple copies of the polypeptide unit with adjacent polypeptide units being linked by an intraconnecting linker, the polypeptide unit being one copy of a product peptide or multiple copies of the product peptide with adjacent product peptide copies being linked by an intraconnecting linker.

3. A method for production of a polypeptide product through expression and purification of a protein purification construct of three, tandem, coupled segments, the first segment being a binding protein, the second segment being an interconnecting linker, and the third segment being a variable fused polypeptide, comprising:

inserting into a compatible host cell an expression vector carrying a recombinant gone having base segments coding for the segments of the protein purification construct to produce a transformed host cell;

causing the transformed host cells to express the protein purification construct;

obtaining a mixture of the protein purification construct with other cellular constituents from the transformed host cells;

contacting the mixture with an immobilized ligand for the binding protein to produce a bound protein purification construct conjugated to the immobilized ligand;

removing unbound cellular constituents from the bound protein purification construct to produce a segregated protein purification construct;

treating the segregated protein purification construct with a cleavage agent for the interconnecting linker to produce a free variable fused polypeptide and recovering the free, variable fused polypeptide as the polypeptide product, wherein;

the binding protein is mammalian or human carbonic anhydrase, or a modified version of the mammalian or human carbonic anhydrase the modified version of the carbonic anhydrase a) has an amino acid sequence that is free at least of the segment for the interconnecting linker, b) has a dissociation constant for a mammalian or human carbonic anhydrase inhibitor that is no more than about $10^{-7}M$, and c) the amino acid sequence of the modified version of carbonic anhydrase is the amino acid sequence of human or mammalian carbonic anhydrase that has been modified by a change selected from the group consisting of: elimination of methionine residues, replacement of one or more glutamate residues with another amino acid residue, replacement of one or more arginine residues with another amino acid residue, replacement of one or more asparagine residues with another amino acid residue, replacement of one or more methionine residues with another amino acid residue, replacement of one or more cysteine residues with another amino acid residue, and any combination thereof; and, the immobilized ligand is an inhibitor for mammalian or human carbonic anhydrase or the modified version of mammalian or human carbonic anhydrase; and, the variable fused polypeptide is a single polypeptide unit or multiple copies of the polypeptide unit with adjacent polypeptide units being linked by an intraconnecting linker, the polypeptide unit being one copy of a product peptide or multiple copies of the peptide product with adjacent product peptide copies being linked by an innerconnecting linker.

4. A method according to claim 1 or 3 comprising the additional step of selecting the appropriate transformed host cell after insertion.

5. A method according to claim 1 or 3 wherein the causing step is accomplished by incubating the transformed host cells and inducing the expression of the protein purification construct.

6. A method according to claim 1, 2 or 3 wherein variable fused polypeptide is a single polypeptide unit containing one copy of the product peptide.

7. A method according to claim 1, 2 or 3 wherein the variable fused polypeptide is multiple polypeptide units each containing a single copy of a product peptide, wherein adjacent polypeptide units are linked together by an intraconnecting linker.

8. A method according to claim 1, 2 or 3 wherein the binding protein is the modified version of human or mammalian carbonic anhydrase.

9. A method according to claim 8 wherein the replacements are selected from the group consisting of:

glutamate residue replaced by aspartate residue, arginine residue replaced by lysine residue, asparagine residue replaced by glutamine residue, methionine residue replaced by alanine or lysine residue and cysteine residue replaced by serine residue.

10. A method according to claim 1, 2 or 3 wherein the interconnecting linker, the intraconnecting linker, and the innerconnecting linker contain up to about 10 amino acid residues.

11. A method according to claim 2 or 3 wherein the segregated protein purification construct is bound to the immobilized ligand when it is treated with the cleavage reagent.

12. A method according to claim 11 wherein the variable fused polypeptide is separated from the cleavage reagent.

13. A method according to claim 2 or 3 wherein the treatment step includes disassociating the segregated, protein purification construct from the immobilized ligand to produce a debound protein purification construct; treating the debound protein purification construct with immobilized cleavage regent to produce a mixture of variable fused polypeptide and binding protein joined to at least part of the interconnecting linker, and again contacting the mixture with immobilized ligand to remove the binding protein joined to at least part of the interconnecting linker and produce the purified variable fused polypeptide.

14. A method to claim 2 or 3 wherein the inhibitor is a benzene sulfonamide derivative.

15. A method according to claim 1, 2 or 3 wherein the interconnecting linker, the intraconnecting linker, and the innerconnecting linker are individually and distinguishably selected from the group consisting of (Asp)$_4$Lys, IleGluGlyArg, ArgGlyProArg, ArgGlyGly, AsnGly, AspPro, Met, AspGly, HisProPheHisLeuLeuValTyr, Lys, Arg, Phe, Tyr, Trp, Cys and Glu.

16. A method according to claim 2 or 3 wherein the variable fused polypeptide is multiple polypeptide units each containing a single copy of a product peptide, wherein adjacent polypeptide units are linked together by an intraconnecting linker, and the recovering step comprises cleaving the intraconnecting linker with a second cleavage enzyme or chemical to produce multiples of the product peptide.

17. A method according to claim 1, 2 or 3 wherein the interconnecting linker does not constitute an amino acid sequence that is found in the binding protein or variable fused polypeptide.

18. A method according to claim 2 or 3 wherein the treating step produces a mixture of variable fused polypeptide joined to some amino acid residues from the interconnecting linker and binding protein joined to some amino acid residues from the interconnecting linker; and after the binding protein joined to some amino acid residues from the interconnecting linker is removed, the variable fused polypeptide joined to some amino acid residues from the interconnecting linker is treated with exopeptidase to remove the amino acid residues and produce the purified variable fused polypeptide.

19. A method according to claim 1, 2 or 3 wherein the product peptide is selected from the group consisting of interferon, an antibody fragment, cecropin, an apidaecin, collagen binding protein, an assembled antibody, a sweetening polypeptide, a hormone polypeptide, an enzyme, a structural polpeptide, and a neuropolypeptide.

20. A method according to claim 19 wherein the product peptide is a hormone polypeptide selected from the group consisting of caltrin, calcitonin, vasopressin, oxytocin, an interleukin, angiotensin, insulin, erythropoietin and a mood altering polypeptide.

21. A method according to claim 19 wherein the product peptide is an enzyme selected from the group consisting of tissue plasminogen activator, and a lysozyme.

22. A method according to claim 19 wherein the product peptide is an antibody fragment selected from the group consisting of an antibody light or heavy chain, $F_{ab}$, $F(_{ab})_2$, $F_c$, and a VL or VH antibody fragment.

23. A method according to claim 1, 2 or 3 wherein the product peptide is a cytotoxic polypeptide selected from the group consisting of an antibiotic, an insecticide, an herbicide and a fungicide.

24. A method according to claim 1, 2 or 3 wherein the product peptide is a growth hormone releasing factor, a nerve growth factor or ACTH.

25. A method according to claim 24 wherein the product peptide is a growth hormone releasing factor which is LH—RH.

* * * * *

UNITED STATES PATENT AND TRADEMARK OFFICE
CERTIFICATE OF CORRECTION

PATENT NO. : 5,595,887
DATED : Jan. 21, 1997
INVENTOR(S) : Coolidge et al.

It is certified that error appears in the above-identified patent and that said Letters Patent is hereby corrected as shown below:

In column 34, claim 1, line 5, "units" should read --unit--.

In column 36, claim 19, line 66, insert --a-- after the word fragment,

Signed and Sealed this

Twenty-eighth Day of April, 1998

Attest:

BRUCE LEHMAN

Attesting Officer

Commissioner of Patents and Trademarks